United States Patent [19]

Mishina

[11] Patent Number: 5,555,965
[45] Date of Patent: Sep. 17, 1996

[54] BATTERY OPERATED VENDING MACHINE FOR DISPENSING CYLINDRICAL AND TETRAHEDRON-SHAPED OBJECTS

[76] Inventor: Koji Mishina, 23-15-Imazaike Cho, Toyonaka City, Osaka, Japan

[21] Appl. No.: 424,147

[22] Filed: Apr. 17, 1995

[51] Int. Cl.⁶ .................................................. G07F 11/10
[52] U.S. Cl. ............................. 194/217; 221/129; 221/6
[58] Field of Search ................................ 221/6, 17, 124, 221/129, 131, 185, 199, 258, 266, 274; 194/206, 207, 216, 217, 218, 350, 351

[56] References Cited

U.S. PATENT DOCUMENTS

| | | |
|---|---|---|
| 364,028 | 5/1887 | MacBeth . |
| 937,820 | 10/1909 | Ladue . |
| 1,452,721 | 4/1923 | Antoine . |
| 1,585,179 | 5/1926 | Whipple . |
| 1,610,001 | 12/1926 | Foster . |
| 1,802,629 | 4/1931 | Copeland . |
| 3,161,321 | 12/1964 | Mellion et al. . |
| 3,445,037 | 5/1969 | Rothbaum ........................ 221/266 X |
| 3,785,509 | 1/1974 | Girardi . |
| 4,109,825 | 8/1978 | Weitzman . |
| 4,301,909 | 11/1981 | Snavely . |
| 4,308,974 | 1/1982 | Jones ................................ 221/266 X |
| 4,405,059 | 9/1983 | Kull ....................................... 221/129 |
| 4,526,264 | 7/1985 | MacNamara et al. . |
| 4,872,591 | 10/1989 | Konopka ........................... 221/129 X |
| 5,092,489 | 3/1992 | Pastor et al. ..................... 221/258 X |
| 5,127,543 | 7/1992 | Meisels ............................. 221/258 X |
| 5,152,422 | 10/1992 | Springer . |
| 5,167,345 | 12/1992 | Bleeker ................................. 221/17 |
| 5,316,124 | 5/1994 | Barnes et al. . |

OTHER PUBLICATIONS

Catalog No. P-9306 145M Jan. 1, 1993, Bobrick Washroom Equipment, Inc.
Catalog No. P-9406 100M Jan. 1, 1994, Bobrick Washroom Equipment, Inc.

*Primary Examiner*—Karen B. Merritt
*Assistant Examiner*—Scott L. Lowe
*Attorney, Agent, or Firm*—Troutman Sanders LLP

[57] ABSTRACT

A compact, battery-operated vending machine dispenses cylindrical and tetrahedron-shaped objects. More specifically, the inventive vending machine may be placed in public bathrooms for dispensing feminine articles such as cylindrical and pad-type tampons. The vending machine includes at least one rotary dispensing mechanism for dispensing cylindrical objects. A product stack of cylindrical objects feeds into the rotary dispensing assembly, which feeds the cylindrical objects into a dispensing area for access by the consumer. The vending machine also includes at least one plunger dispenser assembly for dispensing tetrahedron-shaped objects into the dispensing area. The vending machine also includes a sensor for sensing product depletion of product stacks above each dispenser, actuators for displaying "sold-out" signs for each dispenser upon product depletion, and a mechanism for blocking a coin slot upon product depletion in all dispensers.

21 Claims, 14 Drawing Sheets

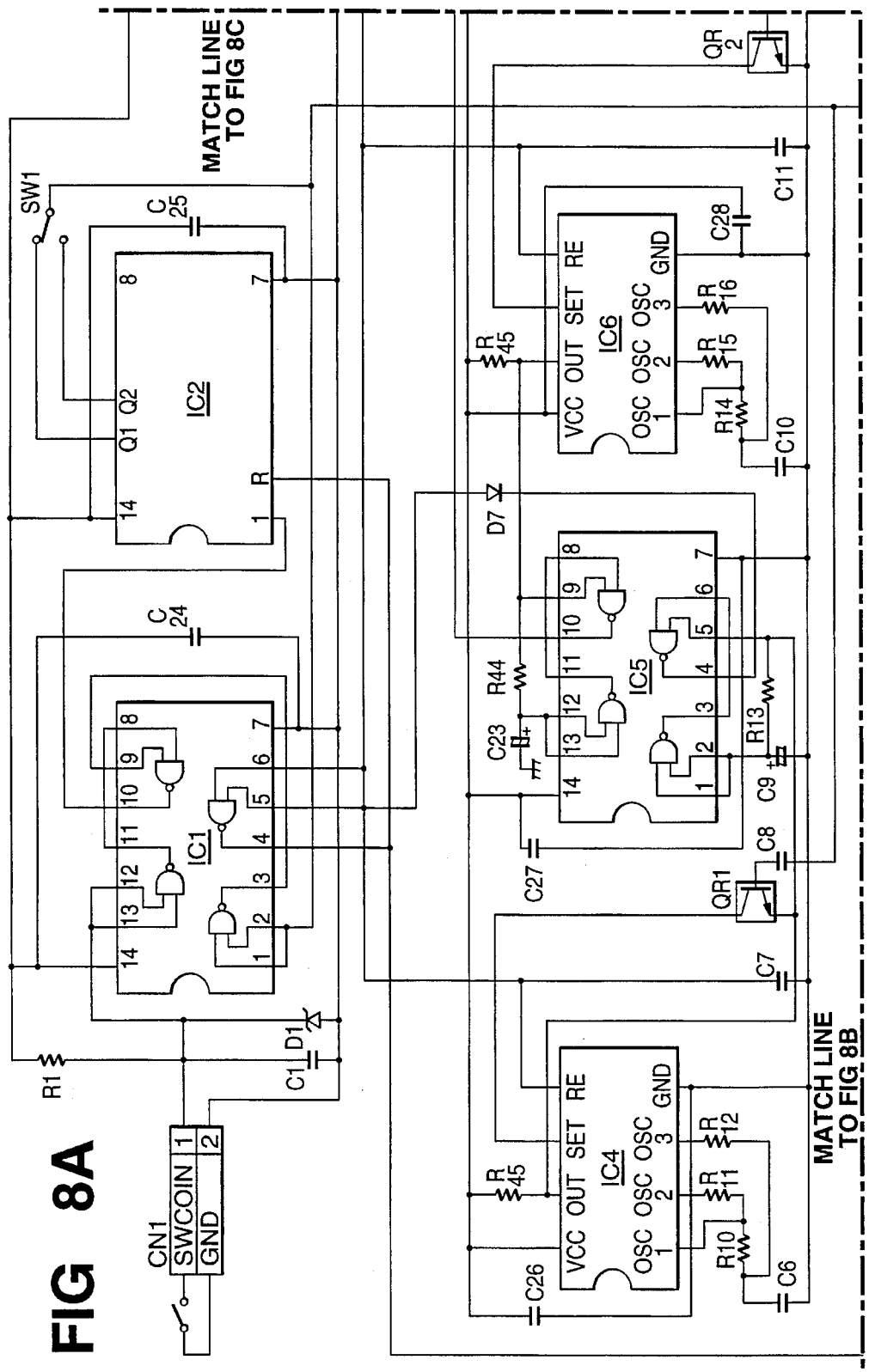

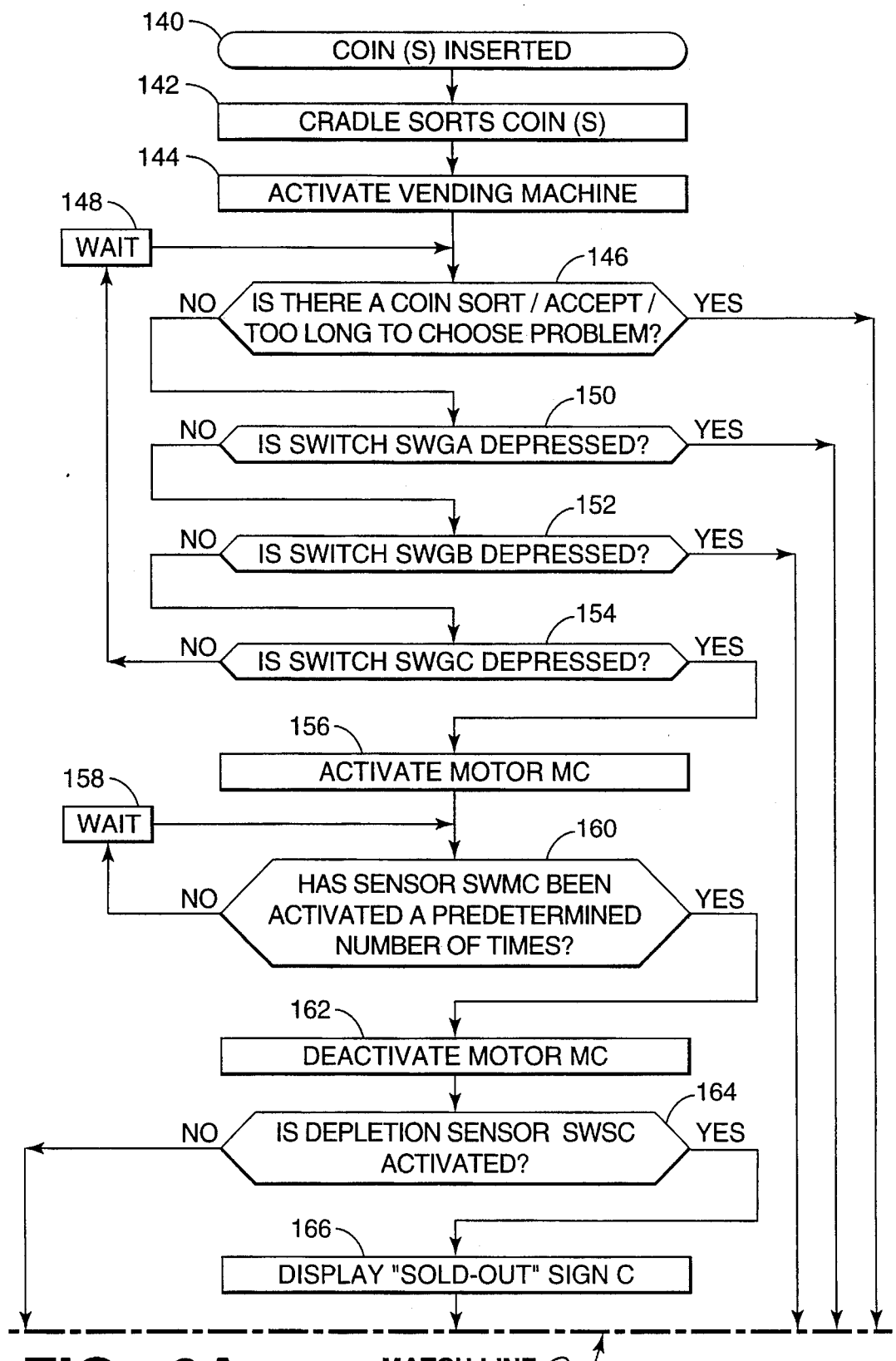
FIG 9A  MATCH LINE TO FIG 9B

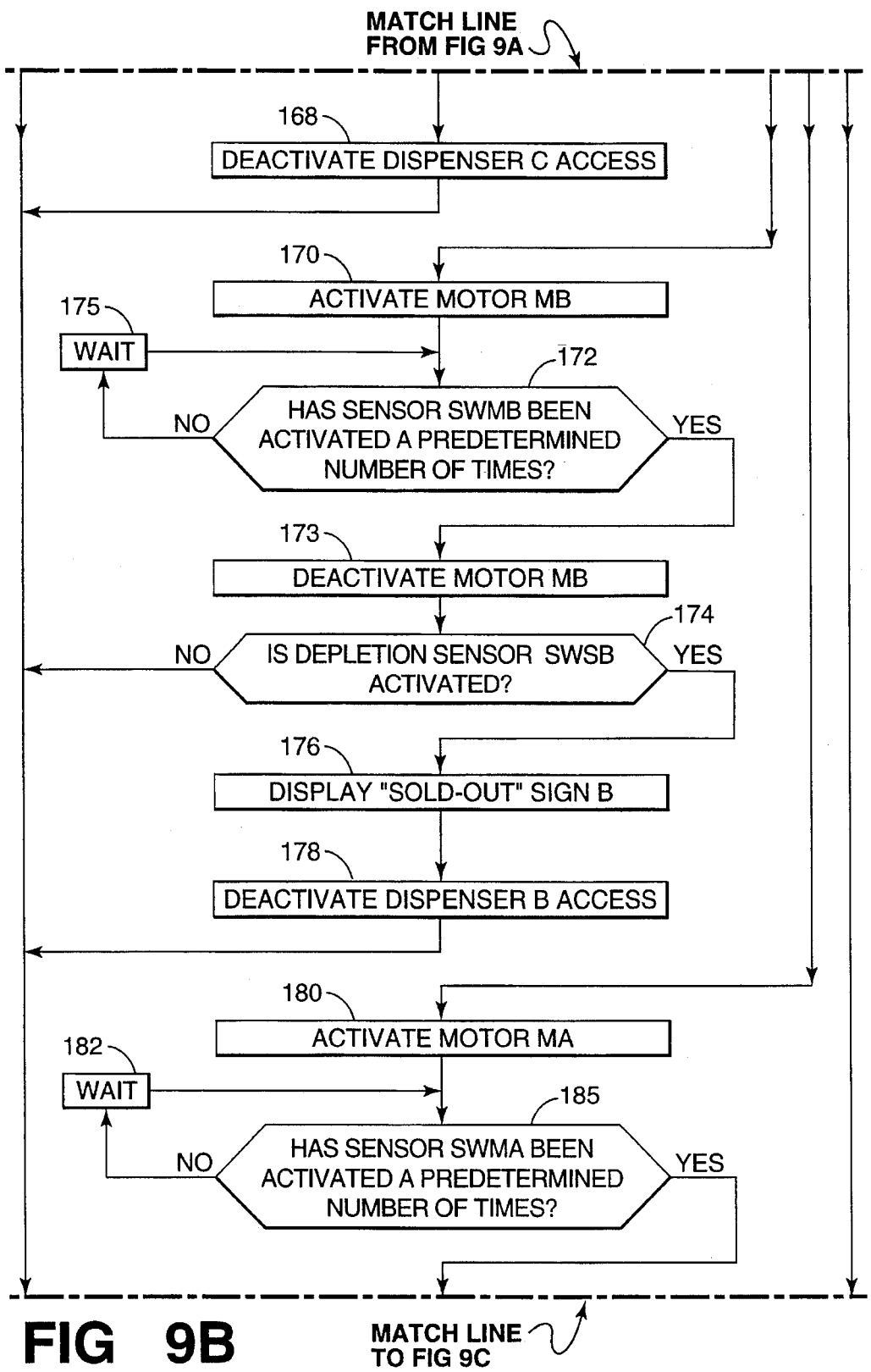

BATTERY OPERATED VENDING MACHINE FOR DISPENSING CYLINDRICAL AND TETRAHEDRON-SHAPED OBJECTS

BACKGROUND OF THE INVENTION

1. Technical Field

This invention relates generally to vending machines, and more particularly, battery operated, microprocessor controlled vending machines which dispenses cylindrical and tetrahedron-shaped objects.

2. Description of the Prior Art

U.S. Pat. Nos. 3,785,509, 3,161,321, 1,802,629, 1,610,001, and 1,585,179, disclose machines which utilize rotary dispensing devices. For example, U.S. Pat. No. 1,585,179 discloses a pencil vending machine including a pair of rollers which receive pencils from storage magazines. Longitudinally extending grooves on each of the rollers feed pencils into a dispensing area. Additionally, U.S. Pat. Nos. 1,610,001 and 1,802,629 disclose cigarette vending machines which also utilize cylindrical rotors for transferring cigarettes from a magazine to a dispensing area. Finally, U.S. Pat. No. 3,785,509 discloses a transfer device which includes a cylindrical rotor for placing work pieces into a holding device positioned on a conveyor.

There are several disadvantages associated with the above-referenced prior art rotary dispensing devices. First, many of the rotary dispensing devices require manual operation. Depending upon the vending machine size, those who have little hand strength find it difficult to operate such vending machines. Furthermore, consumers and vending machine operators generally desire electronically actuated machines over manually operated machines since electronic machines usually accept a wide variety of coins and paper currency, electronic machines have a more modern appearance, and electronic machines utilize easy-to-operate selection buttons. However, electronic vending machines usually require a standard electrical outlet for power to operate dispensing mechanisms and currency recognition devices. This power requirement limits the locations in which they may be placed, and therefore limits the number of possible locations of such machines.

SUMMARY OF THE INVENTION

The present invention recognizes and addresses the foregoing disadvantages, and others of prior art constructions and methods.

Accordingly, it is an object of the present invention to provide a reliable, easily operated vending machine which requires little maintenance other than periodic refilling with product packages.

It is another object of the present invention to provide a vending machine which is operable in virtually any location, regardless of the availability of standard electrical outlets.

It is another object of the present invention to provide a battery powered, microprocessor controlled vending machine for automatic control of dispensing product packages.

Still another object of the present invention is to provide a vending machine which includes a motor-operated rotary dispensing mechanism in combination with plunger-type mechanisms which all dispense products into a common dispensing area.

Still another object of the present invention is to provide a vending machine having selection buttons which require as little pushing pressure as possible so that consumers having less-than-average hand strength or prosthetic limbs may easily select a product.

Still another object of the present invention is to provide a microprocessor controlled rotary dispenser which automatically dispenses one cylindrical package per cycle.

Finally, another object of the present invention is to provide a vending machine which utilizes as little power as possible during operation and between dispensing cycles.

Generally speaking, the invention relates to a vending machine for dispensing virtually any type of product. Preferably, the inventive vending machine may vend health-related products such as cylindrical tampons, pad-like tampons, condoms, or any other product commonly used in health maintenance. The inventive vending machine may utilize battery-powered, microprocessor controlled dispensers to dispense products. Thus, a vending operator may locate the inventive vending machine in virtually any location, regardless of power outlet location.

More particularly, the vending machine according to the present invention includes a housing for protecting internal components and vending products, various types of dispensers for vending products, and control means responsive to consumer input for controlling the dispensers during dispense cycles. Furthermore, the inventive vending machine may include a currency slot adapted to accept currency for a product and a currency sensor adapted to sense when a predetermined amount of currency has been detected. The vending machine may also include at least one selector switch associated with the dispensers, wherein the switch is adapted to send a dispense signal the control means for dispensing a product.

The dispensers within the inventive vending machine may include rotary and plunger-type dispensing mechanisms for dispensing products. For example, the vending machine may include at least one rotary dispenser assembly adapted to accept and rotatingly dispense products from a gravity feed compartment positioned above the rotary dispenser assembly. Additionally, the vending machine may include at least one plunger assembly adapted to laterally displace products from a product stack located above the plunger assembly.

More specifically, the plunger assembly may include a motor, a laterally collapsible mechanical linkage coupled to the motor, and a plunger coupled to the linkage for displacing a bottom-most product from a product stack above the plunger assembly into a dispensing chamber during a dispense cycle.

The rotary dispensing assembly may include a motor for driving the rotary dispensing assembly and a cylindrical rotor adapted to receive products from a product column disposed above the rotary dispensing assembly for dispensing products into the dispensing chamber during a dispense cycle.

The vending machine also includes a common dispensing chamber for receiving objects from each of the dispenser assemblies. In a preferred embodiment, the inventive vending machine includes two plunger dispensers for laterally dispensing products into the dispensing chamber. Preferably, lateral sides of the dispensing chamber include the plunger dispensers. Additionally, a preferred embodiment of the present invention may also include the rotary dispenser located between the plunger dispensers and above the dispensing chamber.

The dispensing chamber of the present invention may include two side walls disposed opposite one another, wherein each the sidewalls includes a plunger assembly disposed on an outside portion thereof. Furthermore, each sidewall includes a side wall aperture adapted to receive a product from the plunger assembly. The dispensing chamber also includes a top portion defined by the rotary dispenser assembly and a front opening adapted to allow a consumer to obtain a dispensed product from the chamber.

The inventive vending machine may also include control means adapted to control vending machine operations in response to accepting currency and other input from a consumer. More specifically, the control means is responsive to a dispense signal from a product selector switch and a currency signal from the currency sensor for initiating a dispense cycle. In a first embodiment, a first selector switch may be associated with the plunger dispensers, and a second selector switch may be associated with the rotary dispenser, wherein the first and second selector switches send a dispense signal to the control means for initiating a dispense cycle when a consumer deposits a correct amount of currency. In the first embodiment, the rotary dispenser may dispense a first type of product, while the plunger dispenser each dispense a second type of product. Thus, only one switch may necessarily be associated with each type of dispenser.

In a second embodiment, each dispenser may include a selector switch for sending a dispense signal to the control means. In this embodiment, each dispenser contains a different type of product, and the control means is responsive to the dispense signal and the currency signal for initiating a dispense cycle in a dispenser corresponding with a particular selector switch.

The inventive vending machine may also include a depletion sensor in each dispenser for detecting product depletion and for sending a product depletion signal to the control means. The control means samples the depletion sensor after initiating a product dispense cycle in a dispenser. Additionally, the control means is responsive to the depletion signal from a depletion sensor for deactivating a dispenser. Additionally, the control means may be responsive to the depletion signal for activating means for displaying a "sold-out" sign associated with each dispenser. Finally, control means is responsive to depletion signals from all of the dispensers for deactivating the vending machine and for activating means for blocking the coin slot.

Other objects, features and aspects of the present invention are discussed in greater detail below.

BRIEF DESCRIPTION OF THE DRAWINGS

The accompanying drawings illustrate the preferred embodiment of the invention, and serve to aid in the explanation of the principles of the invention.

FIGS. 8A–8D illustrate a schematic circuit diagram of the electronic portions of the vending machine as illustrated in FIG. 1, showing specific examples of microcontroller means, sensor means, and electronic portions of the plunger assembly and rotary dispenser assembly.

FIGS. 9A–9C illustrate an operational flow chart showing the operation of the microcontroller means illustrated in FIGS. 7 and 8A–8D of the vending machine according to the present invention.

DETAILED DESCRIPTION OF THE INVENTION

Mechanical Layout

Figure 1:
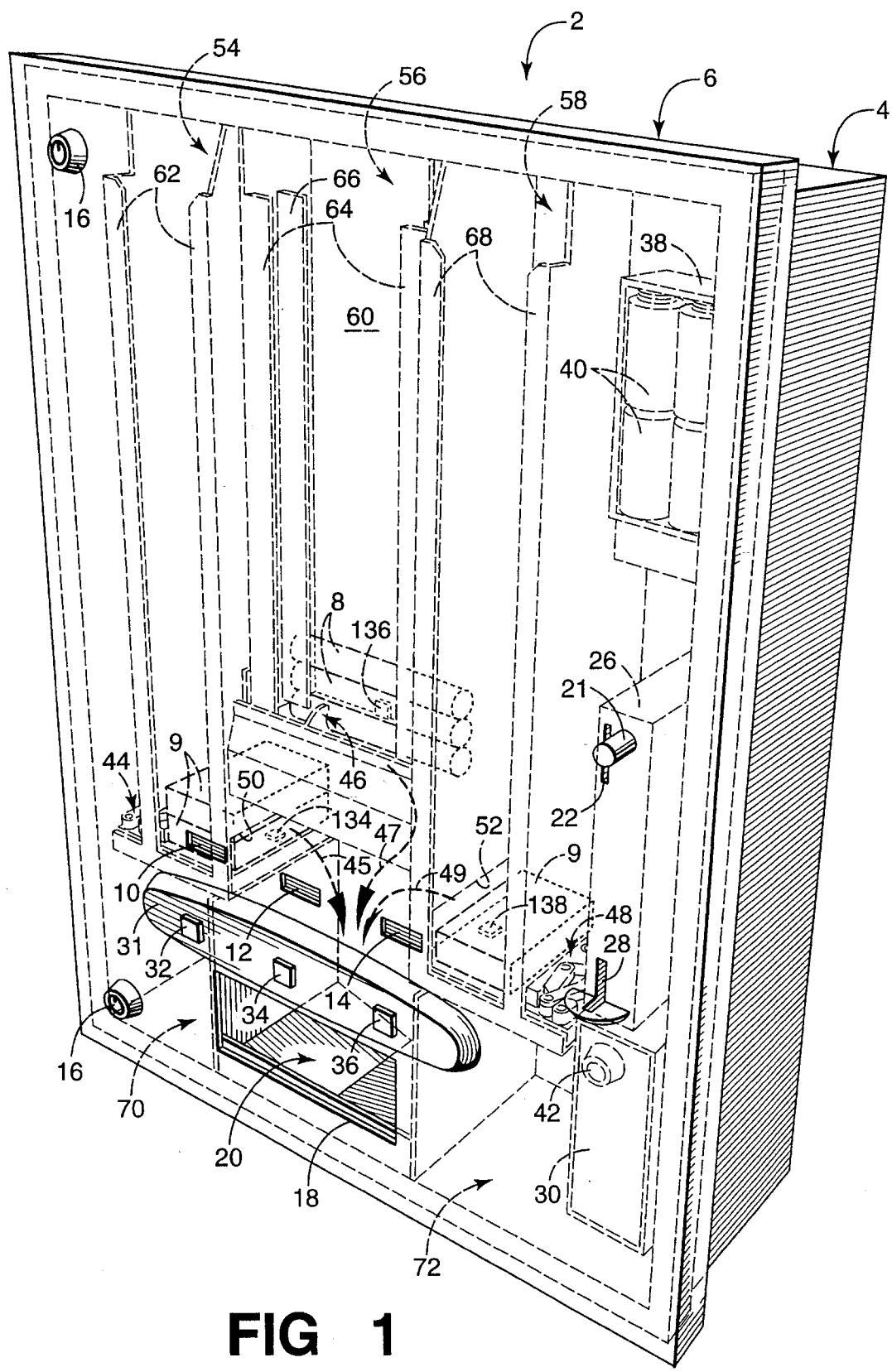
FIG. 1 illustrates a perspective view of the vending machine according to the present invention with an interior portion of the vending machine generally represented by hidden lines.

FIG. 1 illustrates the inventive vending machine which is generally indicated by reference numeral 2. Vending machine 2 includes an outer housing 4 which is preferably fabricated from sheet metal, or any other suitable material for housing inner portions of the vending machine. Housing 4 includes a front panel 6 rotatably attached to the cover by any suitable hinge element (not shown). Front panel 6 allows easy access to inner portions of vending machine 2 for refilling product packages, mounting, and routine maintenance, as is explained in further detail below. As is seen in FIG. 1, vending machine 2 may be mounted so that housing 4 is recessed into a wall, thereby only exposing front panel 6. Alternatively, bolts or other fastening means (not shown) may simply fasten a rear wall of housing 4 to a wall of an appropriate location for vending machine 2.

Although vending machine 2 may be any size appropriate for the type of package to be dispensed, a preferred embodiment of the inventive vending machine includes an overall housing 4 having a width of approximately 514 millimeters (mm), a height of approximately 692 mm, and a depth of approximately 127 mm. A vending machine according to the present invention having the preferred size as enumerated above dispenses a product from dispensers 44 and 48 having a width of approximately 45 mm, a depth of approximately 45 mm, and a height of approximately 13 mm. Additionally, the inventive vending machine having the preferred size as enumerated above may dispense a cylindrical object from dispenser 46 having a length of 100 mm and a diameter of 10 mm. Although dispenser 46 preferably dispenses a cylindrical objects, dispenser may 46 an object having virtually any shape as long as the object fits with column 56 and the rotor mechanism. Furthermore, the product columns 54, 56, and 58 may be adapted to store products of virtually any shape or size.

Locking mechanisms 16 allow a technician to access the vending machine interior while providing adequate security against vandals and thieves. Front panel 6 may include an area which displays product advertising material identifies a product type associated with each dispenser unit and corresponding selector button.

Front panel 6 includes a merchandise coin slot 22 for accepting currency in exchange for a product package dispensed by the vending machine. Hidden lines in FIG. 1 also illustrate a coin sorting mechanism 26 which sorts currency and detects when an appropriate amount of currency has been inserted into the vending machine for purchasing a product. As explained in further detail below, the coin sorting mechanisms may depress a microswitch or trip an optical device which activates the vending machine to dispense a product into dispensing area 20 for a consumer. Return button 21 actuates the sorting mechanism to return coinage within the sorting mechanism. Hidden lines in FIG. 1 also illustrate a coin bin 30 which receives all coins passing through the coin sorting mechanism 26. Coin bin 30 also includes a coin bin lock 42 for security.

An upper right hand corner of housing 4 also includes battery pack 38, batteries 40, and related electronics stored behind the battery pack. Functional characteristics of the control electronics as well as a specific example of electronic componentry are described in greater detail below. Although any type of battery or energy cell may be used, a preferred embodiment of the present invention utilizes four (4) 1.5 volt size "D" battery cells 40 for adequate power. It should be noted, however, that power for the inventive vending machine may be derived from any standard electrical power outlet source, however, battery power does not require that the vending machine be located near an electrical outlet, thus allowing the inventive vending machine to be mounted in virtually any location.

A lower portion of panel 6 includes a button panel 31 which includes push buttons 32, 34, and 36. As is explained in further detail below, push button 32 corresponds to plunger dispenser 44, 34 to rotary dispenser 46, and 36 to plunger dispenser 48. Each push button requires less than one half pounds of pushing force to be depressed, thus allowing those with little hand strength or prosthetic arms and hands to easily select the product they desire. This electronic button configuration is extremely important since the Americans for Disabilities Act now requires that many vending machines have selector buttons that are easily depressed. Furthermore, the Americans for Disabilities Act also prohibits the use of vending machines having lever arms, twisting selectors, or any other selector mechanism which is not easily operated by a person having less-than-average hand strength or a person having prosthetic limbs.

"Sold-out" indicators 10, 12, and 14 are disposed above push buttons 36, 34, and 32, respectively. As discussed in greater detail below, when a dispenser depletes the products in its supply column or malfunctions, control means within the vending machine activates respective "sold-out" signs for that particular column and deactivates the dispenser. The vending machine may activate the "sold-out" signs in a variety of ways. For instance, the vending machine may illuminate the "sold-out" signs upon product depletion in a particular column with a light emitting diode (LED), a low wattage bulb, or other appropriate illuminating means. Alternatively, the vending machine may activate a sign to fall within a display area with a solenoid-like mechanism upon product depletion. Although illumination means are preferred, virtually any appropriate mechanism may display a "sold-out" sign upon product completion in a particular column.

Below button panel 31, front aperture 18 in panel 6 provides access to dispensing chamber 20, which receives products from each of dispensers 44, 46, and 48. Specifically, plunger dispenser 44 includes a plunger which displaces a product through lateral aperture 50 and into chamber 20 for access by a consumer, as arrow 45 illustrates. Similarly, arrow 49 illustrates product movement as plunger dispenser 48 displaces products through lateral aperture 52 and into chamber 20. Additionally, arrow 47 illustrates product movement as rotary dispenser 46 dispenses product downward into chamber 20. The dispenser mechanisms are discussed in greater detail below.

Product storage compartments 54, 56, and 58 store stacks of products above dispensers 44, 46, and 48, respectively. Each storage compartment also feeds products into the dispensing mechanisms via gravitational force. Compartment 54 generally includes lateral and back walls as well as front retaining walls 62 which retain a product stack within the compartment while allowing a technician to view the compartment and reload it if necessary. Similarly, compartment 58 includes retaining walls 68 for that same purpose.

In a preferred embodiment, compartment 56 generally includes two separate chambers defined by front walls 64, intermediate walls 66, sidewalls, and a back wall 60, as is illustrated in FIG. 1. Intermediate walls 66 and rear wall 60 form a rear portion of compartment 56 and hold a rear stack of products while front walls 64 and intermediate walls 66 hold a front stack of products. Although the preferred embodiment of the present invention dispenses cylindrical products from compartment 56, compartment 56 may store other oblong or appropriately shaped objects.

Finally, the spacial configuration of dispensers within the inventive vending machine allows for several storage compartments 70 and 72 to be located laterally of dispensing chamber 20. Storage compartments 70 and 72 may store additional products when compartments 54, 56, and 58 are entirely full. Additionally, compartments 70 and 72 may also store spare battery cells and other replacement components for the vending machine.

Figure 2:
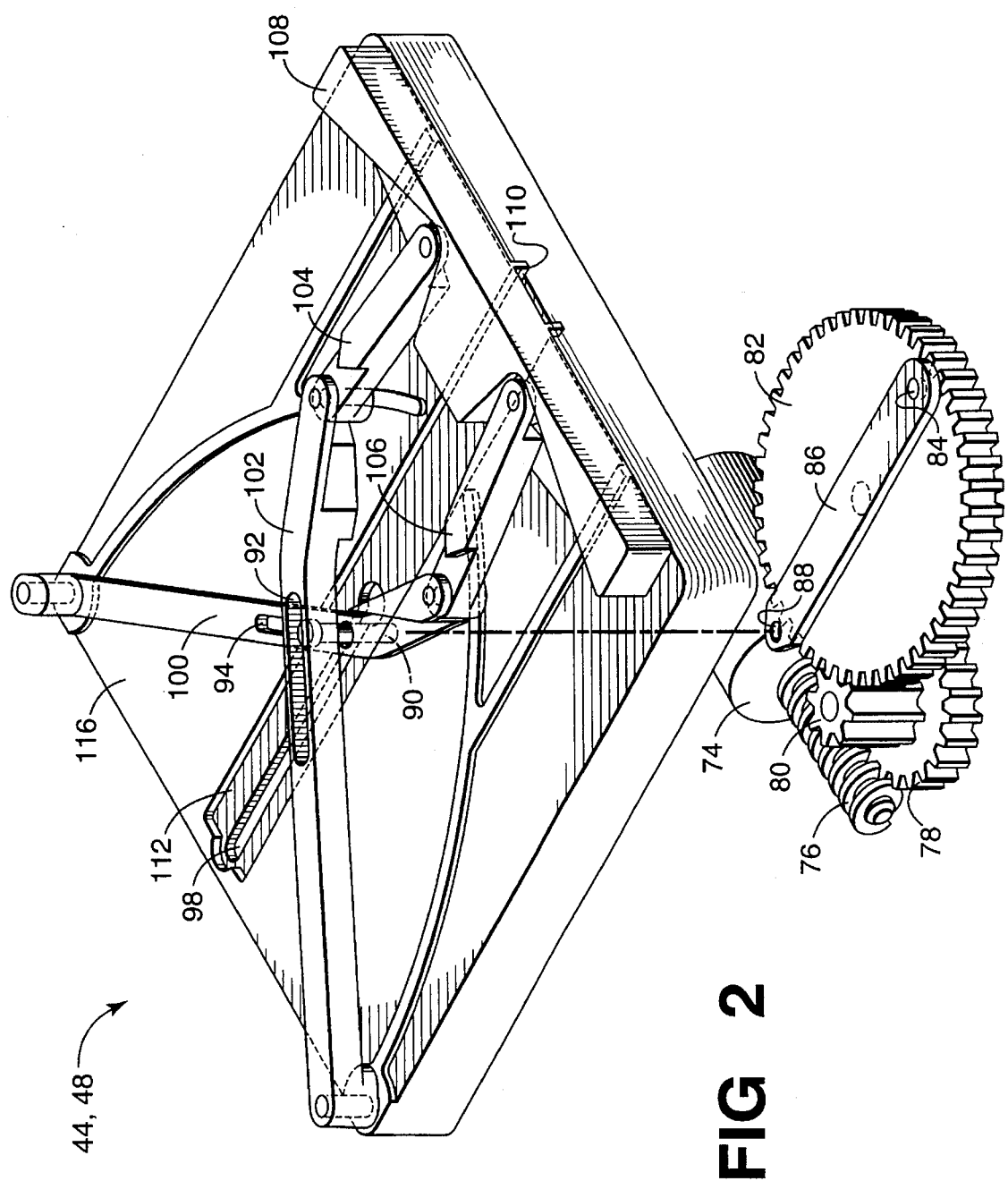
FIG. 2 illustrates an isolated view of a plunger mechanism in an extended position within the inventive vending machine.

FIG. 2 illustrates a specific example and the preferred embodiment of the plunger dispensers 44 and 48 schematically illustrated in FIG. 1. The plunger assembly includes a plunger motor 74 which drives spiral gear 76. Spiral gear 76 engages pinion 78, which is concentric with pinion 80. Pinion 80 drives gear 82. Gear 82 rotates on its center and drives drive arm 86 through pin 84, which allows the drive arm to be rotatingly mounted onto gear 82. Pin 90 couples drive arm 86 to a six bar linkage for reciprocating plunger 108.

A dispenser base 116 secures the motor and drive linkage, and serves as a first linkage between long arms 100 and 102. Long arms 100 and 102 comprise the second and third members of the six bar linkage. Mounting pins rotatably mount long arms 100 and 102 to base 116. Short arms 106 and 104 comprise the forth and fifth members of the six bar linkage, and mounting pins rotatably link short arms 106 and 104 to long arms 100 and 102, respectively. Finally, mounting pins rotatably mount opposite ends of short bars 106 and 104 to plunger 108. Plunger 108 comprises the sixth member of the six bar linkage.

Base 116 also includes drive pin guide 98 which constrains the freedom of motion of pin 90, long arms 100 and 102, and drive bar 86 by engaging long arm slots 92 and 94 and pin guide 90. Additionally, a top surface of base 116 includes a plunger recess 112 which matingly engages a plunger guide 110 disposed on a bottom portion of plunger 108. Guide 110 and recess 112 insure a smooth reciprocating motion of plunger 108. The plunger guide and recess also consistently maintain a front surface of plunger 108 in a position which is parallel to a front edge of base 116 regardless of location of drive bin 90 within drive pin guide 98.

Figure 3A:
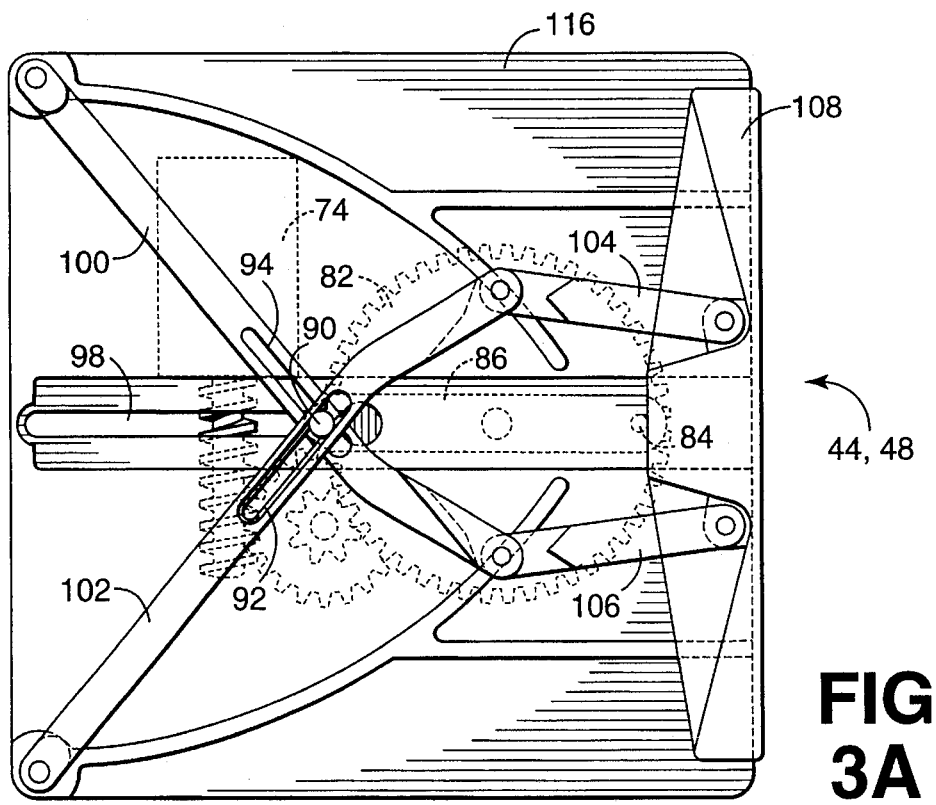
FIG. 3A illustrates a plan view of the plunger of FIG. 2 in an extended position.
Figure 3B:
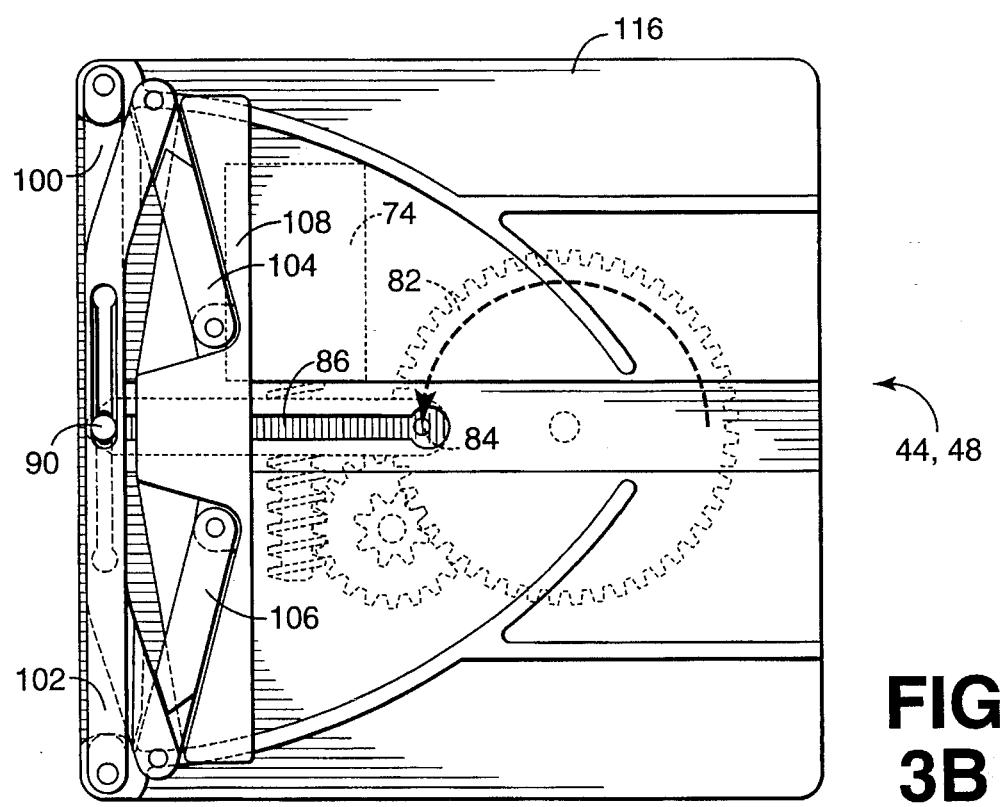
FIG. 3B illustrates a plan view of the plunger of FIG. 2 in a contracted position.

FIGS. 3A and 3B illustrate the interaction between the rotation of gear 82, linear motion of drive arm 86, and the expansion and contraction of the six bar linkage which reciprocates plunger 108. Referring now to FIG. 3A, hidden lines illustrate gear 82 beneath base 116. Additionally, plunger 108 occupies a forward-most position as its resting position between cycles. This forward-most position closes lateral apertures 50 and 52 and prevents access by thieves or vandals to the stack of products above the plunger assembly.

Upon implementation of a dispense cycle, motor 74 rotates gear 82 in a counterclockwise motion through the series of gears between the motor shaft and gear 82, as explained above. In the resting position, drive arm 86 lies across a complete diameter of gear 82 and positions drive 90 in a forward-most position within the drive pin guide 98. As gear 82 rotates in a counterclockwise direction, drive arm 86 translates the rotational motion of gear 82 into a linear motion of drive pin 90 toward a rearward portion of drive pin guide 98. As drive pin 90 move rearward, it rotates long arms 100 and 102 toward a back edge of base 116 through slots 92 and 94. Forward ends of long arms 100 and 102 then rotate away from each other and each move in a rearward direction during rearward motion of drive pin 90, which causes rearward ends of short arms 104 and 106 to move laterally outward with respect to their anchored positions on plunger 108, and rearward with respect to a forward edge of base 116, thereby moving plunger 108 into a rearward direction.

FIG. 3B illustrates the plunger 108 in mid-completion of a dispense cycle. Plunger 108 occupies a rearward-most position in the dispense cycle while the six-bar linkage is in a collapsed position. As gear 82 continues to rotate, drive arm 86 then pulls pin 90 in forward motion, thus causing the six-bar linkage to expand by engagement with the long arm slots 92 and 94 until plunger 108 moves into its forward-most position and dispenses a product through one of lateral apertures 50 or 52. Plunger 108 remains in a forward-most position until implementation of another dispense cycle.

Figure 4A:
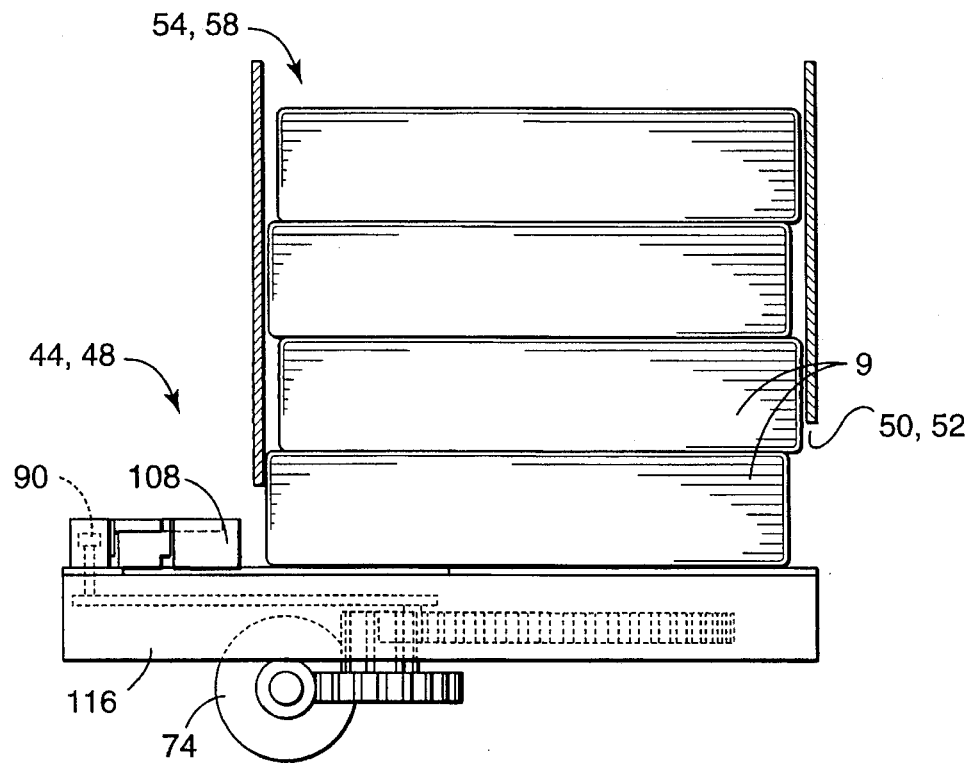
FIG. 4A–4B illustrate a plunger mechanism of FIGS. 3A and 3B dispensing a product during a dispense cycle.
Figure 4B:
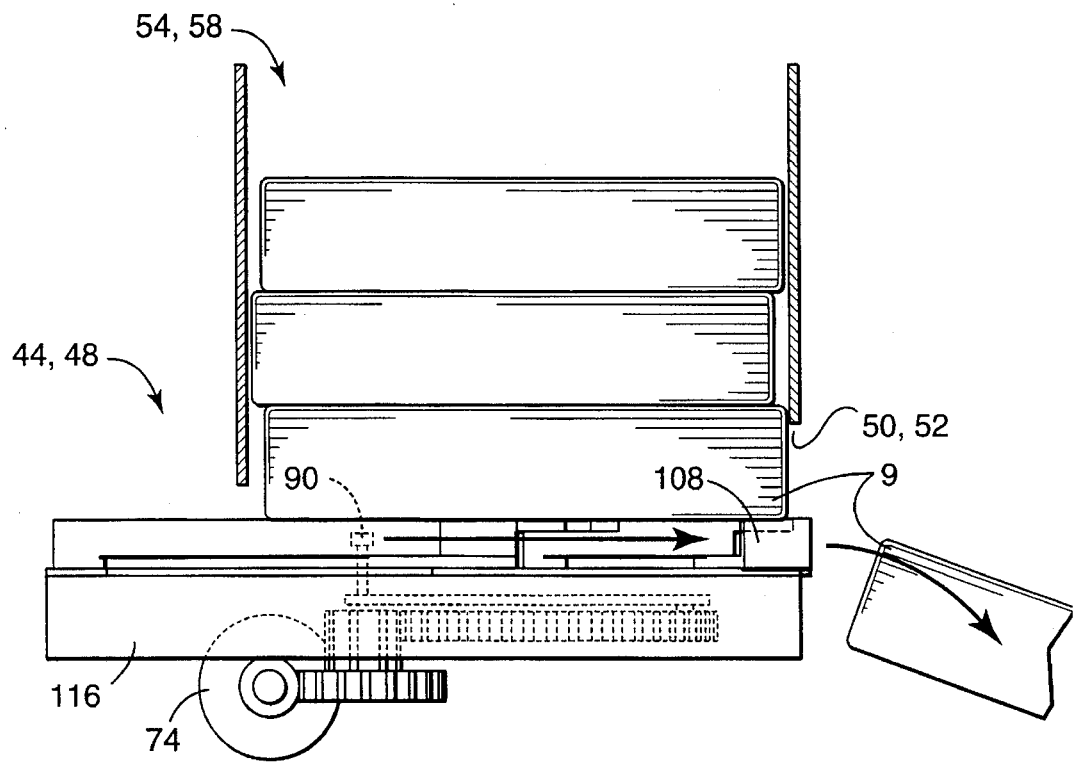

FIGS. 4A and 4B illustrate a product stack above the plunger dispenser during a dispense cycle. Upon implementation of a dispense cycle by the vending machine control means, plunger 108 moves from a forward-most position as illustrated in FIG. 3A, to a rearward-most position as illustrated in FIGS. 3B and 4A, thereby allowing the product to drop down onto the base 116 within compartments 54 or 58. Plunger 108 then moves toward a forward position and displaces a bottom-most product 9 from the stack and through apertures 50 or 52.

Plunger 108 remains in its forward-most position between dispense cycles, thereby preventing removal of products by a vandal or thief between cycles. As seen in FIG. 4B, the thickness of the plunger assembly raises a top edge of a bottom-most product package in the stack of products above a top edge of lateral apertures 50 and 52. That arrangement prevents the bottom-most package from being removed until dispensed during a product dispense cycle.

Each plunger dispenser also includes depletion sensors 134 and 138 (see FIG. 1) located near the stack of products within the vending machine for detecting when plunger dispensers 44 and 48 deplete product compartments 54 and 58. Depletion sensors 134 and 138 may comprise a plurality of devices such as strategically placed microswitches which detect complete product depletion, a piezoelectric sensor for sensing lack of product, optical sensors for sensing lack of product, or any other device which accomplishes the task of signalling the vending machine control means that the plunger dispensers have depleted product in their respective compartments.

The six-bar mechanical linkage illustrated in FIGS. 3A and 3B allows a maximum displacement of plunger 108 while allowing the linkage to be compactly collapsed laterally of the product stack. That arrangement conserves internal space, reduces the required size of the housing, and allows additional room within the housing for other important components, such as the rotary dispenser.

Figure 5:
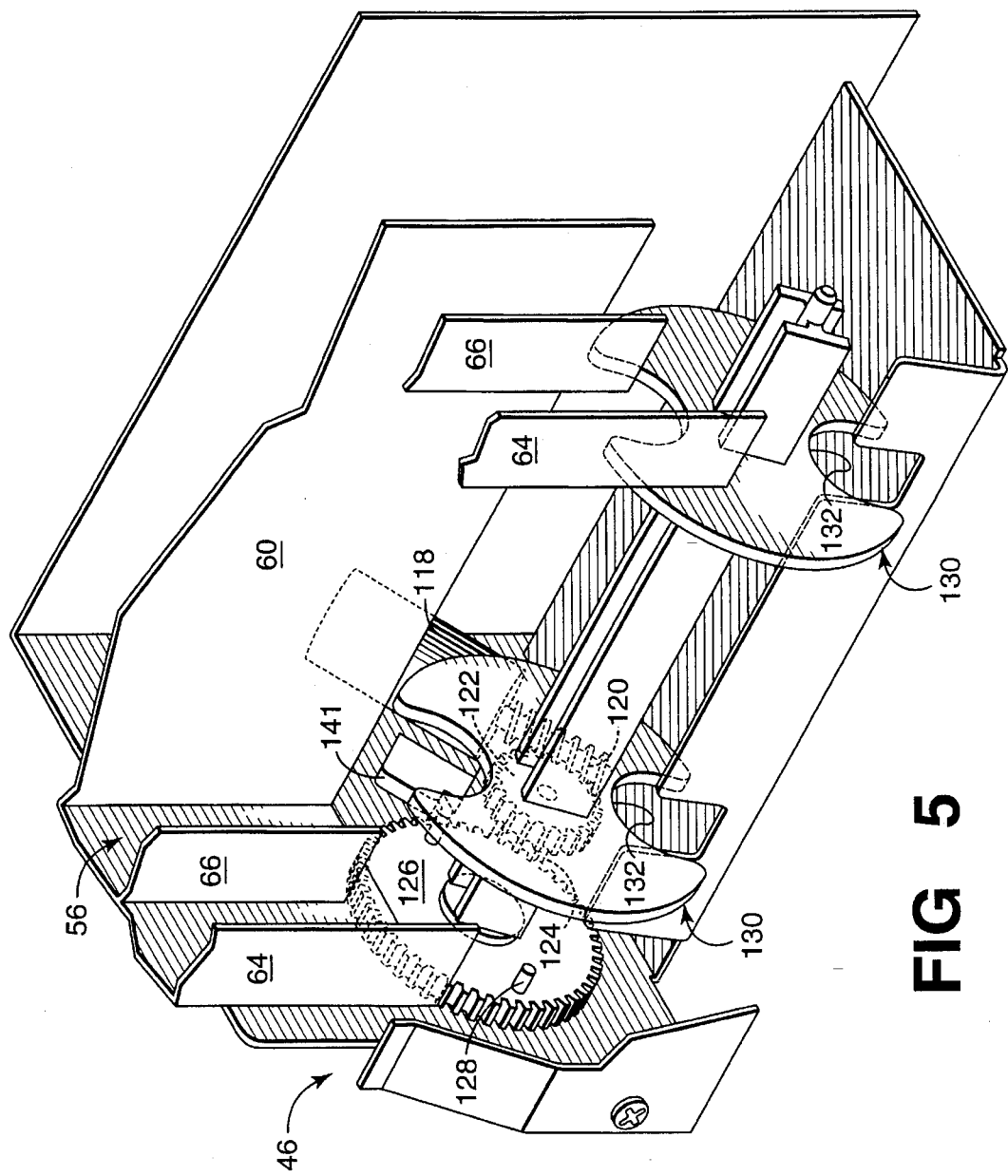
FIG. 5 illustrates an isolated perspective view of a rotary dispenser mechanism of the vending machine in accordance with the present invention.

FIG. 5 illustrates in greater detail the rotary dispenser 46 in accordance with the present invention. Motor 118 rotates spiral gear 120. Spiral gear 120 engages pinion 122 which drives small pinion 124. Pinion 124 engages large gear 126. Large gear 126 drives rotor 130. Rotor 130 includes a pair of recesses 132 which receive products from front and rear portions compartment 56 (as defined by front and intermediate walls 64 and 66) and deliver them to the dispensing chamber.

Gear 126 also includes a protrusion 128 on an inside surface thereof for engaging switch 141, which signals the control means that a complete dispense cycle is about to be completed, as is explained in greater detail below. Additionally, rotary dispenser 46 includes a depletion sensor 136 (see FIG. 1) located near the stack of products within the vending machine for detecting when the rotary dispenser depletes product compartment 56. Depletion sensor 136 may comprise a plurality of devices such as a strategically placed microswitch which detects complete product depletion, a piezoelectric sensor for sensing lack of product, an optical sensor for sensing lack of product, or any other device which accomplishes the task of signalling the vending machine control means the rotary dispenser has depleted products in compartment 56.

Figure 6A:
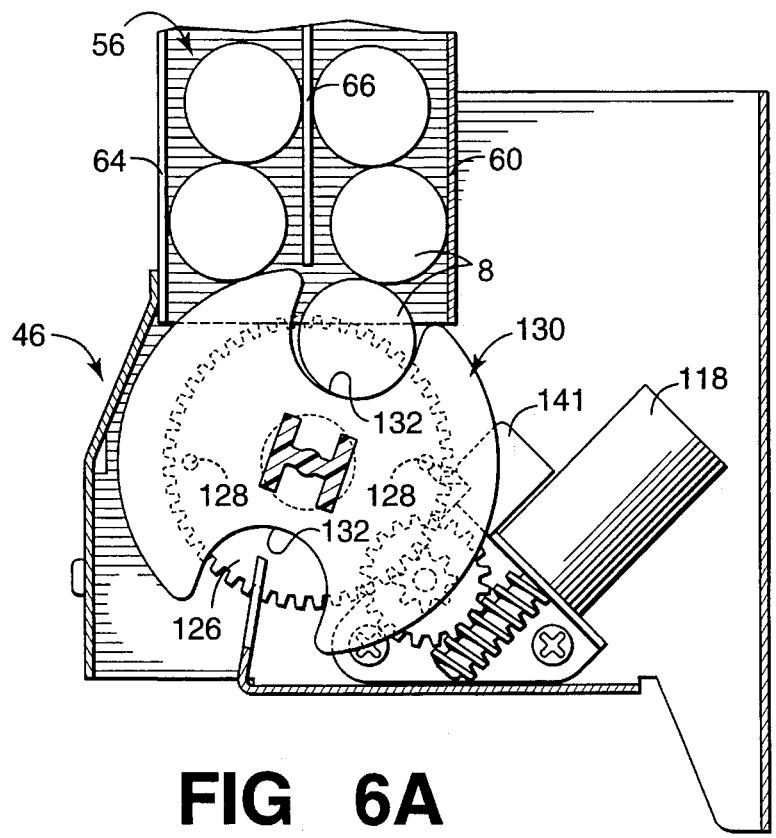
FIG. 6A illustrates a dual compartment positioned above the rotary mechanism, and further illustrates a product dropping into a longitudinal slot within the rotary mechanism.
Figure 6B:
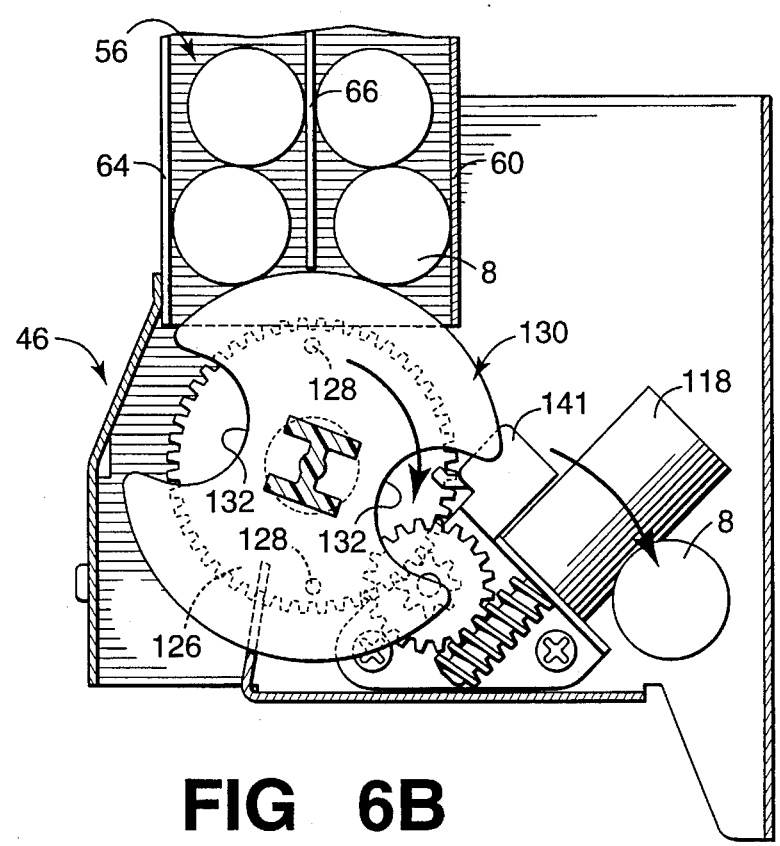
FIG. 6B illustrates the rotary mechanism within the inventive vending machine dispensing a product into a common dispensing area.

FIGS. 6A and 6B illustrate rotary dispenser 46 during a dispense cycle. As rotor 46 rotates clockwise upon commencement of a dispense cycle, a pair of recesses 132 receives a product 8 from a forward portion of compartment 56. Rotor 130 then carries product 8 clockwise within its recesses until the product falls out of the recesses from gravitational forces, as illustrated by 6B. Product 8 then falls into dispensing chamber 20 for access by a consumer. After a pair of recesses has received a product, remaining portions of the rotor prevent other products from falling out of column 56, as is illustrated in FIGS. 6A and 6B.

Since rotor 130 rotates in a clockwise direction, it depletes a forward portion of compartment 56 first. For instance, if a forward portion of column 56 deposits a product into recess 132, when recess 132 passes under a rearward portion of column 56, the product received from the forward portion of the compartment prevents additional products from being received and retains products within the rearward portion of compartment 56. Thus, after the rotary dispenser completely empties the forward chamber, the rearward chamber then deposits products into the recesses 132. This feature also insures delivery of product into rotor 130 from the rearward compartment should the forward compartment become clogged with product.

Electronic and Logic Control Layout

Figure 7:
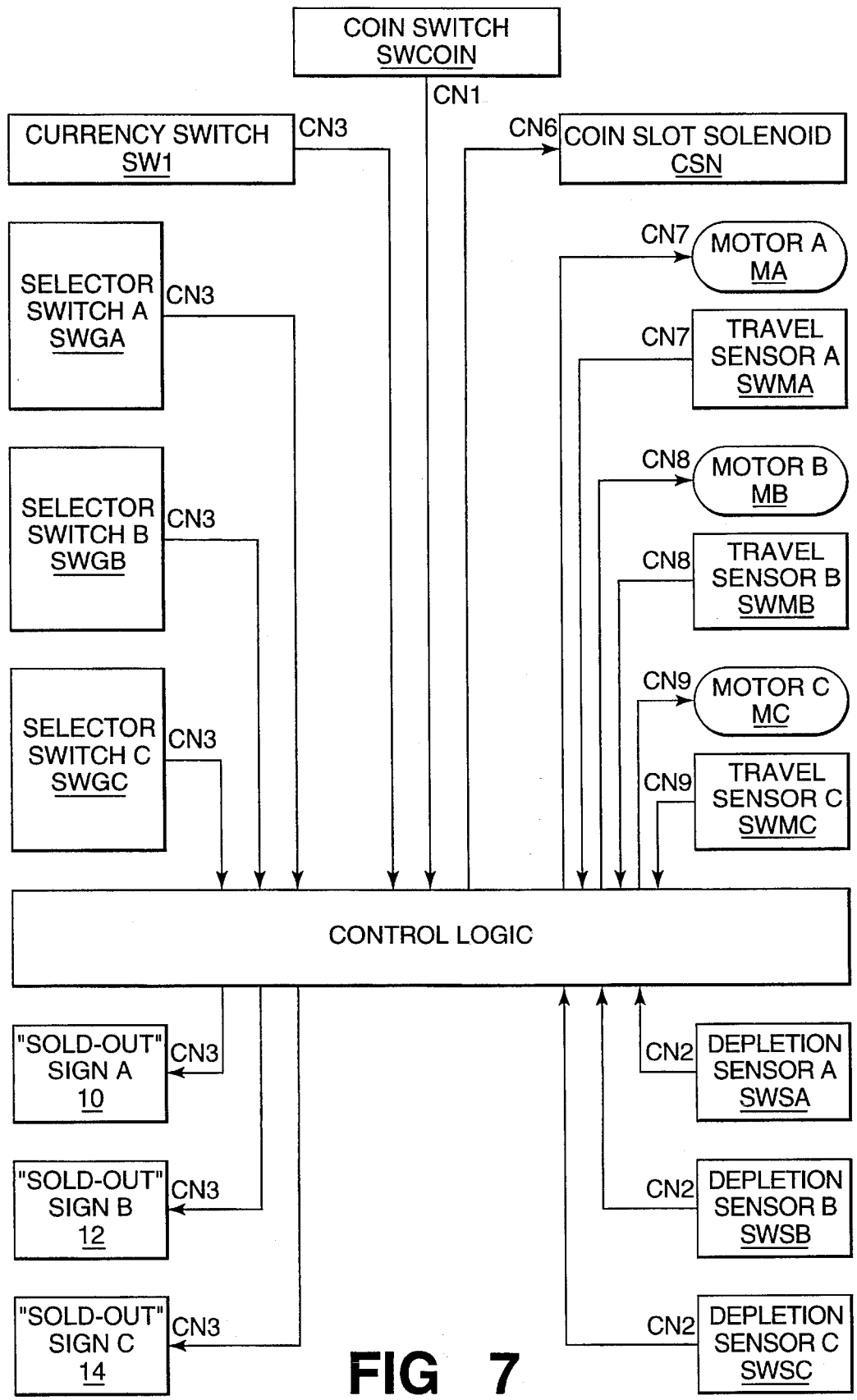
FIG. 7 illustrates a functional circuit block diagram for the electronic portions of the inventive vending machine.
Figure 8B:
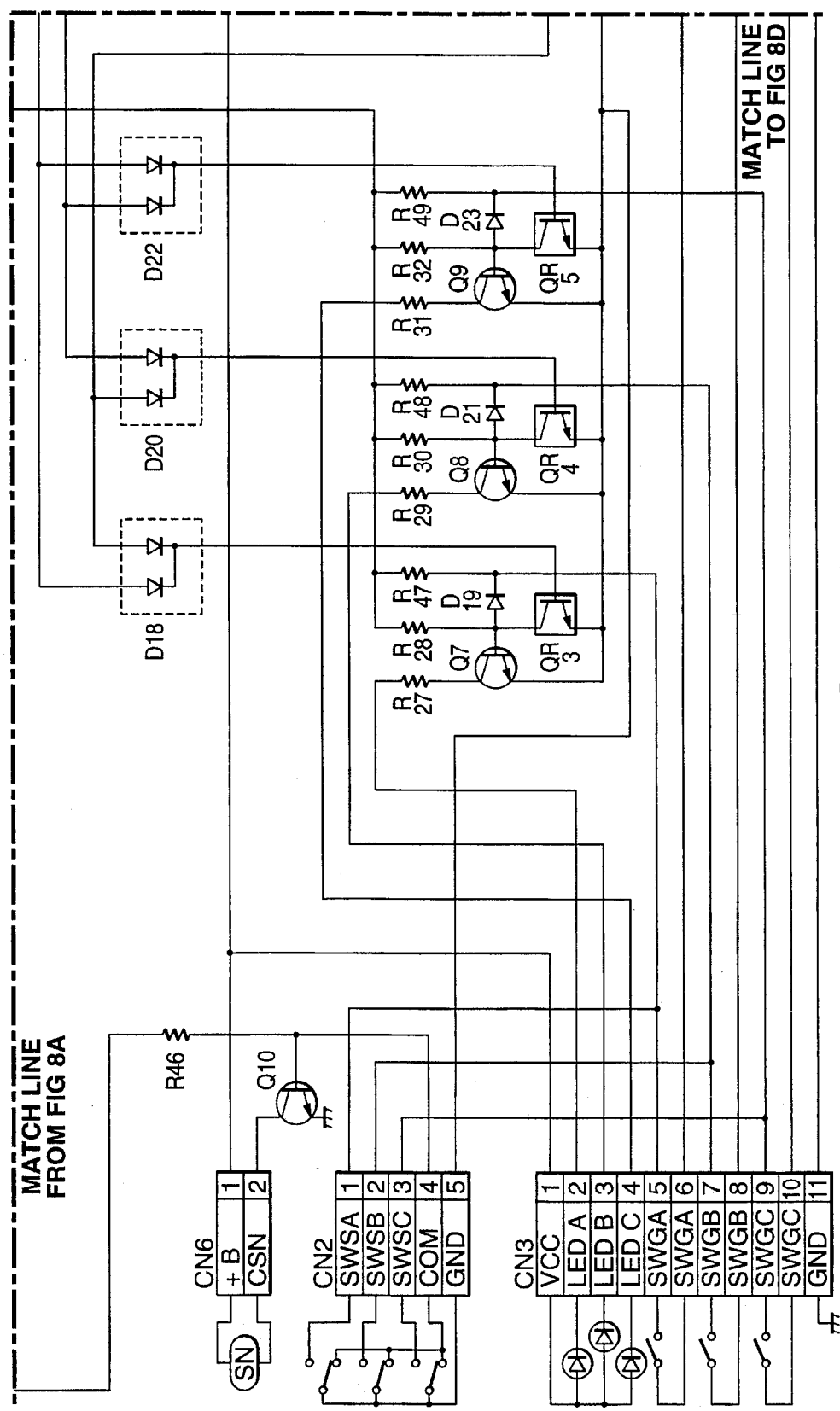
Figure 8C:
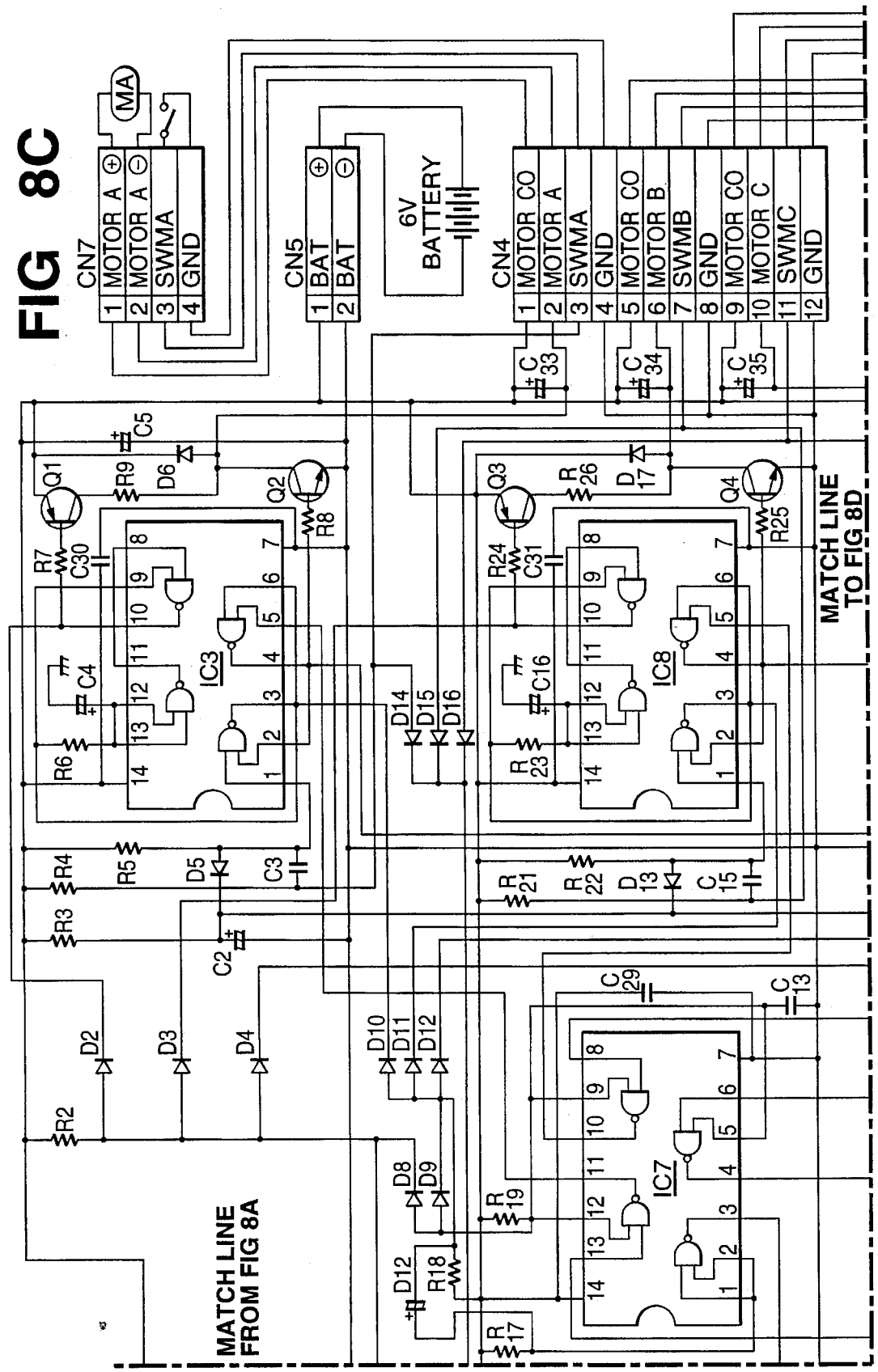
Figure 8D:
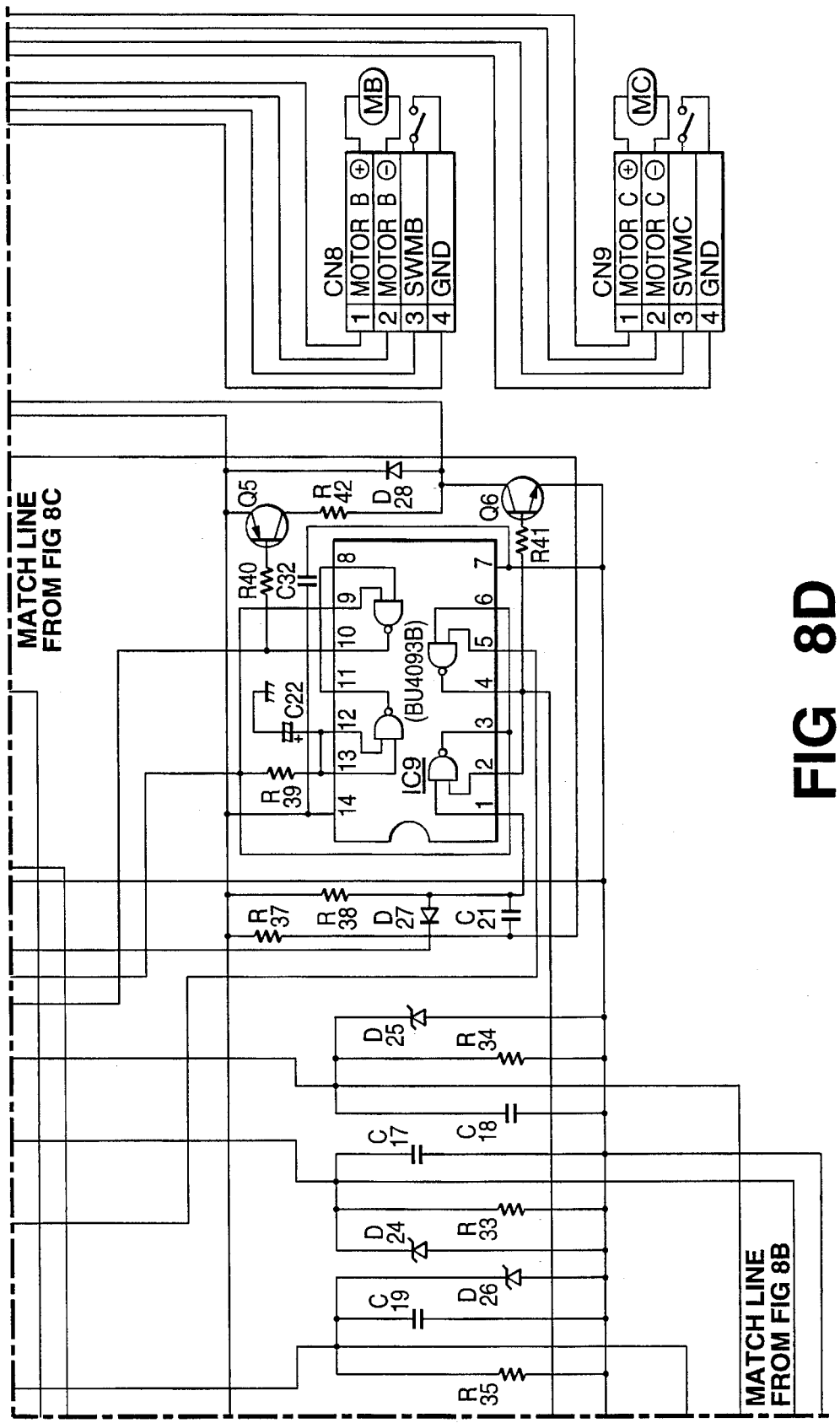

FIG. 7 illustrates a functional block diagram layout for the electronic portions of the inventive vending machine illustrated in FIGS. 8A–8D. Generally, a microcontroller of the present invention is comprised of a combination of integrated circuit chips IC1–IC9. This combination of integrated circuits interfaces with a series of switches and sensors to implement the logic control of the inventive vending machine vending machine. Details of the logic control are illustrated in greater detail in FIGS. 9A through 9c.

Referring now to FIG. 7, the microcontroller interfaces with selection switches SWGA, SWGB, and SWGC through connector CN3. Select buttons 36, 34, and 32 operate switches SWGA, SWGB, and SWGC, respectively. Depletion sensors 134, 136, and 138 each interface with the microcontroller. As discussed above, these sensors may include any type of sensor, however, for the purposes of illustration each of the sensors are represented by microswitches SWSA, SWSB, and SWSC, which open upon product depletion in a particular column, thus signalling the microcontroller to deactivate user access to their respective dispensers.

The microcontroller activates motors MA, MB, and MC through connectors CN7, CN8, and CN9, respectively. Motors MA and MC, which are the plunger dispenser motors, are represented schematically in FIGS. 3(A)–4(B) as motor 74. Motor MB, which is the rotary dispenser motor, is represented in FIGS. 5(A)–6(B) as motor 118. Each of these motors may be of the six (6) volt DC type, or of any other type adapted to power a dispenser. Additionally, the microcontroller interfaces with the motor control switches SWMA, SWMB, and SWMC through connectors CN7, CN8, and CN9, respectively to implement control over each of motors MA, MB, and MC, respectfully, during a dispense cycle. Furthermore, connector CN6 allows the microcontroller to activate the coin mechanism to accept coins and deactivate the coin mechanism to return coins in response to various conditions within the vending machine, as will be discussed in greater detail below.

Connector CN3 allows the microcontroller to activate "sold-out" signs A, B, and C, within spaces 10, 12 and 14, respectively in response to dispensing problems, low battery power, or depletion of products as sensed by depletion sensors 134, 136, and 138. In this particular example, each of the sensors may be embodied as pressure sensitive microswitches SWSA, SWSB, and SWSC which open when dispensers deplete product stacks in storage compartments 54, 56, and 58, respectively. Finally, connector CN1 allows the coin switch SWCOIN to signal the microcontroller to begin a dispense cycle. The coin switch may be mechanical, optical or of any other type for accepting currency and appropriately signalling a microcontroller.

FIGS. 8A–8D illustrate a schematic circuit diagram of the electronic portions of the vending machine as illustrated in FIG. 1, showing specific examples of the microcontroller means, sensor means, and electronic portions of the dispenser assemblies. The circuitry which may be used in one embodiment of the present invention is depicted in the schematic diagram of FIGS. 8A–8D, is discussed below. Several components are shown in FIGS. 8A–8D for implementing the functionality of the vending machine. It will be readily understood that FIGS. 8A–8D disclose merely a preferred embodiment of the present invention, and that other suitable configurations which accomplish the logic control illustrated in FIGS. 9(A)–9(C) may be employed as well.

Referring now to the schematic circuit diagram of FIGS. 8A–8D, the circuit is comprised of integrated circuits IC1 through IC9. Coin switch SWCOIN is connected via connector CN1 to integrated circuit IC1 specifically at pins 13 and 12. Referring to integrated circuit IC1, pins 1 and 2 are each connected to switch SW1, pin 3 is connected to pin 9, pin 8 is connected to pin 11, and pin 12 is connected to pin 13. Pin 14 of integrated circuit IC1 is connected through resistor R1 and capacitor Cl in series to terminal 2 of connector CN1. Additionally, pin 7 of integrated circuit IC1 is connected through capacitor C24 to pin 14.

Referring now to integrated circuit IC2, pin 1 of integrated circuit IC2 is connected to pin 10 of integrated circuit 1, pin R of integrated circuit IC2 is connected to the base portion of transistor Q10, pin 7 of integrated circuit IC2 is connected through capacitor C25 to pin 14 of integrated circuit 2 and pins Q1 and Q2 of integrated circuit IC2 are connected to switch SW1. Additionally, the single pole portion of SW1 is connected to pins 1 and 2 of integrated circuit 1.

Finally, pin 14 of integrated circuit IC2 is connected through resister R1 and capacitor C1 in series to terminal 2 of connector CN2, pin 7 of integrated circuit 2 is connected through capacitor C25 to pin 14, and pin 1 of integrated circuit 2 is connected to pin 10 of integrated circuit 1.

Referring now to integrated circuit IC3, pin 1 is connected to pin 14 of integrated circuit IC2, pin 2 is connected through resister R8 to base portion of transistor Q2, pin 3 is connected to pins 6 and 13 through resistor R6, pin 4 is connected through resistor R8 to base portion of transistor Q2, pin 5 is connected to pin 11 of integrated circuit IC7, pin 7 is connected through capacitor C30 to pin 14, pin 8 is connected to pin 11, pin 9 is connected to pins 3 and 6, pin 10 is connected through resistor 7 to a base portion of transistor Q1, and pin 12 is connected to ground through capacitor C4 and connected to pin 13.

Referring now to integrated circuit IC4, pin VCC is connected through capacitor C26 to the ground pin. Pin OUT is connected through resistor R43 in series to: pin 14 of integrated circuit 5, pin VCC of integrated circuit IC6, pin 1 of integrated circuit IC7 through resister R17 in series, pin 14 of integrated circuit IC7, pin 12 of integrated circuit IC7 through resister R19 in series, pin 14 of integrated circuit ICS, and terminal 1 of connector CN4. Pin OUT of integrated circuit 4 is also connected to pin 5 of integrated circuit IC5. Pin set of integrated circuit IC4 is connected to collector terminal of transistor QR1. Pin OSC3 of integrated circuit IC4 is connected in series through resistors R12 and R10 to pin OSC1, and pin OSC2 is connected in series through a resistor R11 to OSC1. Additionally, pin OSC1 of integrated circuit 4 is connected in series through resistor R10 and capacitor C6 to: the ground terminal of integrated circuit IC4, the emitter terminal of transistor QR1, pin 5 of integrated circuit IC1 through capacitor C7, pin 2 of integrated circuit IC5 through capacitor C9, pin 7 of integrated circuit IC5, pin OSC1 of integrated circuit IC6 through capacitor C10 and resistor R14 in series, pin OSC2 of integrated circuit IC6 through capacitor C10 and resistor R14 and resistor R15 in series, and to pin OSC3 of integrated circuit IC6 through capacitor C10 and resistor R16 in series.

Referring now to integrated circuit IC5, pins 1 and 2 are connected together, pins 3 and 6 are connected together, pins 8 and 11 are connected together, and pins 12 and 13 are connected together. Additionally, pin 7 of integrated circuit IC5 is connected to pin 14 through capacitor C27. Additionally, pin 12 is connected to ground through capacitor C23, and to pin OUT of integrated circuit IC6 through resistor R44.

Referring now to integrated circuit IC6, pin GND is connected through capacitor C28 to pin VCC, pin RE is connected through capacitor C11 to ground, and pin GND of integrated circuit IC6 is connected to pin 7 of integrated circuit IC7. Finally, pin SET of integrated circuit 6 is connected to the collector terminal of transistor QR2.

Referring now to integrated circuit IC7, pins 1 and 2 are connected to each other, pin 1 is connected through resistor R17 and resistor R45 in series to pin OUT of integrated circuit 6, pin 3 is connected to a base terminal of transistor QR2, pin 4 is connected to pin 5 of integrated circuit IC9, pin 5 connected to pin 9, pin 6 connected to terminal 10 of connector CN3, pin 8 is connected to terminal 8 of connector CN3, pin 10 is connected to pin 5 of integrated circuit ICS, and pin 13 is connected to terminal 6 of connector CN3. Additionally, pin 14 of integrated circuit IC7 is connected through resistor R18, diode D12 and resistor R39 to pin 13 of integrated IC9.

Referring now to integrated circuit IC8, pin 1 is connected through resistor R22 to pin 14, pin 2 is connected to pin 4 and a base terminal of transistor Q4 through resistor R25, pin 3 is connected to pins 6 and 9, pin 7 is connected to, pin 14 through capacitor C31. Pin 8 is connected to pin 11. Pin 9 is connected to pins 3 and 6, pin 10 is connected to a base terminal of transistor Q3 through resistor R24, pin 11 is connected to pin 8, pin 12 to pin 13, and pin 13 is connected through resistor R23 to pin 9. Additionally, pin 12 is connected to ground through capacitor C16.

Referring now to integrated circuit IC9, pin 1 is connected to pin 14 through resistor R38, pin 2 is connected to pin 4 and to a base terminal of transistor Q6 through resistor R41, pin 3 is connected to pin 6, to pin 13 through resistor R39, pin 3 is connected to pin 9, pin 7 is connected to pin 14 through capacitor C32 and is also connected to an emitter terminal of transistor Q6.

Each of the connectors CN1–CN9 interface the sensors, the LEDs, the motors, the battery pack and the solenoid as well as the coin switch to the control circuit. Connector CN1 at terminals 1 and 2 connects coins switch SWCOIN to terminals 1 and 2. Connector CN2 interfaces each of the depletion sensors SWSA, SWSB, SWSC in each of the dispensers to the control circuit for control purposes. Each of the depletion sensor switches of one terminal connected to a common terminal 4 on CN2 while terminal 5 of connector CN2 is connected to ground. Common terminal 4 of connector CN2 is connected to a base terminal of transistor Q10 and pins 4 of integrated circuit IC1 and pin R of integrated circuit IC2 through resistor 46. Terminal 3 of connector CN2 is connected to terminal 9 of connector CN3 and a base portion of transistor Q9 through diode 23. Similarly, terminal 2 of connector CN2 is connected to terminal 7 of connector CN3 and to a base portion of transistor Q8 through diode 21. Finally, a first terminal of connector CN2 is connected to terminal 5 of connector CN3 and a base portion of transistor Q7 through diode 19.

Referring now to connector CN3, terminal 1 labelled as VCC is connected to terminal 1 of CN6 and pin 14 of integrated circuit IC9. Terminals 2, 3 and 4 each are connected to separate LEDs for sold out signs A, B and C respectively, and are each tied to a common voltage source VCC at terminal 1. Additionally, terminal 2 is connected to a collector terminal of transistor Q7 through R27, terminal 3 is connected to a collector terminal of transistor Q8 through resistor R29, and terminal 4 is connected to a collector terminal of transistor Q9 through resistor R31. Additionally, terminals 5, 6, 7, 8, 9 and 10 of connector CN3 each interface with select switches SWGA, SWGB and SWGC within to the control circuit. Furthermore, terminal 11 of connector CN3 at one end is connected to ground and at another is tied to capacitor C17 and C18.

Connector CN4 interfaces the control circuit to each of motors A, B and C for the purpose of driving the dispensers within the inventive vending machine. Motors A and B in the preferred embodiment power a plunger dispenser (for example, motor 74 within dispensers 44 and 48 of FIGS. 2–38) while motor C will power a rotary type dispenser (for example, motor 18 within dispenser 36 as disclosed in FIG. 5 of the present invention). Terminal 1 of connector CN4 interfaces terminal 1 of connector CN7 to pin 14 of integrated circuit IC8. Terminal 2 of connector CN4 interfaces terminal 2 of connector CN7 to a collector terminal of transistor Q1 through diode D6. Terminal 3 of connector CN4 interfaces terminal 3 of connector CN7 to integrated circuits IC3 and IC8. Terminal 3 of connector CN4 is connected to pin 14 of integrated circuits IC2 and IC3. Terminal 4 of connector CN4 interfaces terminal 4 of connector CN7 to ground. Terminal 5 of connector CN4 interfaces terminal 1 of connector CN8 to pin 14 of integrated circuits IC3, IC1, and IC2. Terminal 6 of connector CN4 interfaces terminal 2 of connector CN8 to a emitter terminal of transistor Q3 through resistor R26 and also interfaces terminal 2 of connector CN8 to a collector terminal of transistor Q4. Additionally, an emitter terminal of transistor Q4 is tied to ground. Terminal 7 of connector CN4 interfaces terminal 3 of connector CN8 to pin 10 of integrated circuit IC5 through diode D15. Terminal 8 of connector CN4 interfaces terminal 4 of connector CN8 to ground. Terminal 9 interfaces terminal 1 of connector CN9 to pins 14 of integrated circuits IC2 and IC3. Terminal 10 of connector CN4 interfaces terminal 2 of connector CN9 to an emitter terminal of transistor Q5 through resistor R42 and to a collector terminal of transistor Q6. Terminal 11 of connector CN4 interfaces terminal 3 of connector CN9 to pin 14 of integrated circuit IC9.

Connector CN5 interfaces a series of battery cells preferably arranged in a 6 volt configuration to the vending machine logic control circuitry. Additionally, connector CN6 interfaces solenoid CSN for rerouting the coin path in order to return change to the user in the event of malfunction to the driver circuitry. Specifically, terminal 2 of connector CN6 is connected to a collector terminal of transistor Q10, and terminal 1 of connector CN6 is connected to terminal 1 of connector CN3.

Each of connectors CN7, CN8 and CN9 interface motors A, B and C as well as their respective travel sensors SWMA, SWMB and SWMC respectively to the logic control circuit. Specifically, terminal 1 of connector CN7 is interfaced to a positive terminal of motor A, terminal 2 of connector CN7 is interfaced to a negative terminal to motor A, terminal 3 interfaces a first terminal of travel sensor SWMA to the control circuit, while terminal 4 of connector CN7 interfaces a second terminal of the travel sensor SWMA to ground. Similarly, terminal 1 of connector CN8 interfaces a positive terminal of motor MB to the logic control circuit, terminal 2 of connector CN8 interfaces a negative terminal of motor MB to the logic control circuit, terminal 3 of connector CN8 interfaces a first terminal of travel sensor SWMB to the logic control circuit while terminal 4 interfaces a second terminal of travel sensor SWMB to ground. Finally, terminal 1 of connector CN9 interfaces a positive terminal of motor MC to the logic control circuit. Terminal 2 of connector CN9 interfaces a negative terminal of motor MC to the logic control circuit, terminal 3 of connector CN9 interfaces a first terminal of travel sensor SWMC to the control circuit while terminal 4 of connector CN9 interfaces a second terminal of travel sensor SWMC to ground.

The table below illustrates a complete part list for the above referenced circuit, including, where possible, part numbers, component values, and part manufacturers.

| | COMPONENT LIST | | |
| --- | --- | --- | --- |
| SYMBOL NO. | ITEM NAME-NUMERICAL VALUE - UNIT | MANUFACTURER'S MODEL NUMBER | MANUFR'S NAME |
| CN1 | Connector | IL-G-2P-S3T2-E | JAPAN AIRLINES ELECTRIC (JAE) |
| CN2 | Connector | IL-G-5P-S3T2-E | JAE |
| CN3 | Connector | IL-G-11P-S3T2-E | JAE |

-continued

COMPONENT LIST

| SYMBOL NO. | ITEM NAME-NUMERICAL VALUE - UNIT | MANUFACTURER'S MODEL NUMBER | MANUFR'S NAME |
|---|---|---|---|
| CN4 | Connector | IF-G-12P-S3T2-E | JAE |
| CN5 | Connector | IL-G-2P-S3T2-E | JAE |
| CN6 | Connector | IL-G-2P-S3T2-E | JAE |
| SW1 | Slide switch | SLD-12-5 | Shinmei Electric Co. |
| IC1 | Integrated Circuit | BU4093B | Rohm |
| IC2 | Integrated Circuit | μPD74HC4024C | NEC |
| IC3 | Integrated Circuit | BU4093B | Rohm |
| IC4 | Integrated Circuit | BU2305 | Rohm |
| IC5 | Integrated Circuit | BU4093B | Rohm |
| IC6 | Integrated Circuit | BU2395 | Rohm |
| IC7 | Integrated Circuit | BU4093B | Rohm |
| IC8 | Integrated Circuit | BU4093B | Rohm |
| IC9 | Integrated Circuit | BU4093B | Rohm |
| Q1 | Transistor | 2SB1184 | Rohm |
| Q2 | Transistor | 2SD1760 | Rohm |
| Q3 | Transistor | 2SB1184 | Rohm |
| Q4 | Transistor | 2SD1760 | Rohm |
| Q5 | Transistor | 2SB1184 | Rohm |
| Q6 | Transistor | 2SD1760 | Rohm |
| Q7 | Transistor | 2SC4038TL2 | Rohm |
| Q8 | Transistor | 2SC4038TL2 | Rohm |
| Q9 | Transistor | 2SC4038TL2 | Rohm |
| Q10 | Transistor | 2SC4032TL2 | Rohm |
| QR1 | Digital Transistor | DTC144ELTL2 | Rohm |
| QR2 | Digital Transistor | DTC144ELTL2 | Rohm |
| QR3 | Digital Transistor | DTC144ELTL2 | Rohm |
| QR4 | Digital Transistor | DTC144ELTL2 | Rohm |
| QR5 | Digital Transistor | DTC144ELTL2 | Rohm |
| D1 | ZENER DIODE | MTZJT-77 8.2A | Rohm |
| D2 | Diode | 1SS254T-77 | Rohm |
| D3 | Diode | 1SS254T-77 | Rohm |
| D4 | Diode | 1SS254T-77 | Rohm |
| D5 | Diode | 1SS254T-77 | Rohm |
| D6 | Diode | 1SR139-100T-32 | Rohm |
| D7 | Diode | 1SS130 | Rohm |
| D8 | Diode | 1SS254T-77 | Rohm |
| D9 | Diode | 1SS254T-77 | Rohm |
| D10 | Diode | 1SS254T-77 | Rohm |
| D11 | Diode | 1SS254T-77 | Rohm |
| D012 | Diode | 1SS254T-77 | Rohm |
| D13 | Diode | 1SS254T-77 | Rohm |
| D14 | Diode | 1SS254T-77 | Rohm |
| D15 | Diode | 1SS254T-77 | Rohm |
| D16 | Diode | 1SS254T-77 | Rohm |
| D17 | Diode | 1SR139-100T-32 | Rohm |
| D18 | Diode array | DAN215TL3 | Rohm |
| D19 | Diode | 1SS254T-77 | Rohm |
| D20 | Diode array | DAN215TL2 | Rohm |
| D21 | Diode | 1SS254T-77 | Rohm |
| D22 | Diode array | DAN215TL2 | Rohm |
| D23 | Diode | 1SS254T-77 | Rohm |
| D24 | Zener diode | MTZJT-77 8.2A | Rohm |
| D25 | Zener diode | MTZJT-77 8.2A | Rohm |
| D26 | Zener diode | MTZJT-77 8.2A | Rohm |
| D27 | Diode | 1SS254T-77 | Rohm |
| D28 | Diode | 1SR139-100T-32 | Rohm |
| C1 | Multilayer capacitor 0.1 μF 50 V | SR245F104ZB6 | Rohm |
| C2 | Electrolytic capacitor .1 μF 50 V | UMA1HO1OMCA | Nichicon |
| C3 | Multilayer capacitor 0.1 μF 50 V | SR245F104ZB6 | Rohm |
| C4 | Electrolytic capacitor 10 μF 16 V | UMA1C100MCA | Nichicon Corp. |
| C5 | Electrolytic capacitor 100 μF 10 V | UMA1A101MBA | Nichicon Corp. |
| C6 | Multilayer capacitor 1200 P 50 V | SR245A122JB6 | Rohm |
| C7 | Multilayer capacitor 0.1 μF 50 V | SR245F104ZB6 | Rohm |
| C8 | Multilayer capacitor 0.1 μF 50 V | SR245F104ZB6 | Rohm |

-continued

COMPONENT LIST

| SYMBOL NO. | ITEM NAME-NUMERICAL VALUE - UNIT | MANUFACTURER'S MODEL NUMBER | MANUFR'S NAME |
|---|---|---|---|
| C9 | Multilayer capacitor 1 μF 50 V | UMA1H010MCA | Nichicon |
| C10 | Multilayer capacitor 150 PF 50 V | SR245A151JB6 | Rohm |
| C11 | Multilayer capacitor 0.1 μF 50 V | SR245F104ZB6 | Rohm |
| C12 | Electrolytic capacitor 1.5 μF 35 V | UMF1V1RMCH | Nichicon |
| C13 | Multilayer capacitor 0.01 μF 50 V | SR245F103ZB6 | Rohm |
| C15 | Multilayer capacitor 0.1 μF 50 V | SR245F104ZB6 | Rohm |
| C16 | Electrolytic capacitor 10 μF 16 V | UMAJC100MCA | Nichicon |
| C17 | Multilayer capacitor 0.01 μF 50 V | SR245F103AB6 | Rohm |
| C18 | Multilayer capacitor 0.01 μF 50 V | SR245F103ZB6 | Rohm |
| C19 | Multilayer capacitor 0.01 μF 50 V | SR245F103ZB6 | Rohm |
| C21 | Multilayer capacitor 0.1 μF 50 V | SR245F104ZB6 | Rohm |
| C22 | Electrolytic capacitor 10 μF 16 V | UMA1C100MCA | Nichicon |
| C23 | Electrolytic capacitor 1 μF 50 V | UMA1H010MCA | Nichicon |
| C24 | Multilayer capacitor 0.1 μF 50 V | SR245F104ZB6 | Rohm |
| C25 | Multilayer capacitor 0.1 μF 50 V | SR245F104ZB6 | Rohm |
| C26 | Multilayer capacitor 0.1 μF 50 V | SR245F104ZB6 | Rohm |
| C27 | Multilayer capacitor 0.1 μF 50 V | SR245F104ZB6 | Rohm |
| C28 | Multilayer capacitor 0.1 μF 50 V | SR245F104ZB6 | Rohm |
| C29 | Multilayer capacitor 0.1 μF 50 V | SR245F104ZB6 | Rohm |
| C30 | Multilayer capacitor 0.1 μF 50 V | SR245F104ZB6 | Rohm |
| C31 | Multilayer capacitor 0.1 μF 50 V | SR245F104ZB6 | Rohm |
| C32 | Multilayer capacitor 0.1 μF 50 V | SR245F104ZB6 | Rohm |
| C33 | Electrolytic capacitor 1 μF 50 V | UMA1H010MCA | Nichicon |
| C34 | Electrolytic capacitor 1 μF 50 V | UMA1H010MCA | Nichicon |
| C35 | Electrolytic capacitor 1 μF 50 V | UMA1H010MCA | Nichicon |
| R1 | Carbon film fixed resistor 56 KΩ 1/5 W | R20T-24J563 | Rohm |
| R2 | Carbon film fixed resistor 560 KΩ 1/5 W | R20T-24J564 | Rohm |
| R3 | Carbon film fixed resistor 100 KΩ 1/5 W | R20T-24J104 | Rohm |
| R4 | Carbon film fixed resistor 56 KΩ 1/5 W | R20T-24J563 | Rohm |
| R5 | Carbon film fixed resistor 560 KΩ 1/5 W | R20T-24J564 | Rohm |
| R6 | Carbon film fixed resistor 56 KΩ 1/5 W | R20T-24J563 | Rohm |
| R7 | Carbon film fixed resistor 2 KΩ 1/5 W | R20T-24J202 | Rohm |
| R8 | Carbon film fixed resistor 2 KΩ 1/5 W | R20T-24J202 | Rohm |
| R9 | Carbon film fixed | R20T-24J5R1 | Rohm |

-continued

COMPONENT LIST

| SYMBOL NO. | ITEM NAME-NUMERICAL VALUE - UNIT | MANUFACTURER'S MODEL NUMBER | MANUFR'S NAME |
|---|---|---|---|
| | resistor 5.1 Ω 1/5 W | | |
| R10 | Carbon film fixed resistor 56 KΩ 1/5 W | R20T-24J563 | Rohm |
| R11 | Carbon film fixed resistor 1 MΩ 1/5 W | R20T-24J105 | Rohm |
| R12 | Carbon film fixed resistor 220 KΩ 1/5 W | R20T-24J224 | Rohm |
| R13 | Carbon film fixed resistor 56 KΩ 1/5 W | R20T-24J563 | Rohm |
| R14 | Carbon film fixed resistor 30 KΩ 1/5 W | R20T-24J303 | Rohm |
| R15 | Carbon film fixed resistor 1 MΩ 1/5 W | R20T-24J105 | Rohm |
| R16 | Carbon film fixed resistor 220 KΩ 1/5 W | R20T-24J224 | Rohm |
| R17 | Carbon film fixed resistor 56 KΩ 1/5 W | R20T-24J563 | Rohm |
| R18 | Carbon film fixed resistor 56 KΩ 1/5 W | R20T-24J563 | Rohm |
| R19 | Carbon film fixed resistor 56 KΩ 1/5 W | R20T-24J563 | Rohm |
| R21 | Carbon film fixed resistor 56 KΩ 1/5 W | R20T-24J563 | Rohm |
| R22 | Carbon film fixed resistor 560 KΩ 1/5 W | R20T-24J564 | Rohm |
| R23 | Carbon film fixed resistor 56 KΩ 1/5 W | R20T-24J563 | Rohm |
| R24 | Carbon film fixed resistor 2 KΩ 1/5 W | R20T-24J202 | Rohm |
| R25 | Carbon film fixed resistor 2 KΩ 1/5 W | R20T-24J202 | Rohm |
| R26 | Carbon film fixed resistor 5.1 Ω 1/5 W | R20T-24J5R1 | Rohm |
| R27 | Carbon film fixed resistor 390 Ω 1/5 W | R20T-24J391 | Rohm |
| R28 | Carbon film fixed resistor 56 KΩ 1/5 W | R20T-24J563 | Rohm |
| R29 | Carbon film fixed resistor 390 Ω 1/5 W | R20T-24J391 | Rohm |
| R30 | Carbon film fixed resistor 56 KΩ 1/5 W | R20T-24J563 | Rohm |
| R31 | Carbon film fixed resistor 390 Ω 1/5 W | R20T-24J391 | Rohm |
| R32 | Carbon film fixed resistor 56 KΩ 1/5 W | R20T-24J563 | Rohm |
| R33 | Carbon film fixed resistor 100 KΩ 1/5 W | R20T-24J104 | Rohm |
| R34 | Carbon film fixed resistor 100 KΩ 1/5 W | R20T-24J104 | Rohm |
| R35 | Carbon film fixed | R20T-24J104 | Rohm |

-continued

COMPONENT LIST

| SYMBOL NO. | ITEM NAME-NUMERICAL VALUE - UNIT | MANUFACTURER'S MODEL NUMBER | MANUFR'S NAME |
|---|---|---|---|
| R37 | resistor 100 KΩ 1/5 W Carbon film fixed resistor 56 KΩ 1/5 W | R20T-24J563 | Rohm |
| R38 | Carbon film fixed resistor 560 KΩ 1/5 W | R20T-24J564 | Rohm |
| R39 | Carbon film fixed resistor 56 KΩ 1/5 W | R20T-24J563 | Rohm |
| R40 | Carbon film fixed resistor 2 KΩ 1/5 W | R20T-24J202 | Rohm |
| R41 | Carbon film fixed resistor 2 KΩ 1/5 W | R20T-24J202 | Rohm |
| R42 | Carbon film fixed resistor 5.1 Ω 1/5 W | R20T-24J5R1 | Rohm |
| R43 | Carbon film fixed resistor 56 KΩ 1/5 W | R20T-24J563 | Rohm |
| R44 | Carbon film fixed resistor 56 KΩ 1/5 W | R20T-24J563 | Rohm |
| R45 | Carbon film fixed resistor 56 KΩ 1/5 W | R20T-24J563 | Rohm |
| R46 | Carbon film fixed resistor 56 KΩ 1/5 W | R20T-24J563 | Rohm |
| R47 | Carbon film fixed resistor 56 KΩ 1/5 W | R20T-24J563 | Rohm |
| R48 | Carbon film fixed resistor 56 KΩ 1/5 W | R20T-24J563 | Rohm |
| R49 | Carbon film fixed resistor 56 KΩ 1/5 W | R20T-24J563 | Rohm |

Figure 9C:
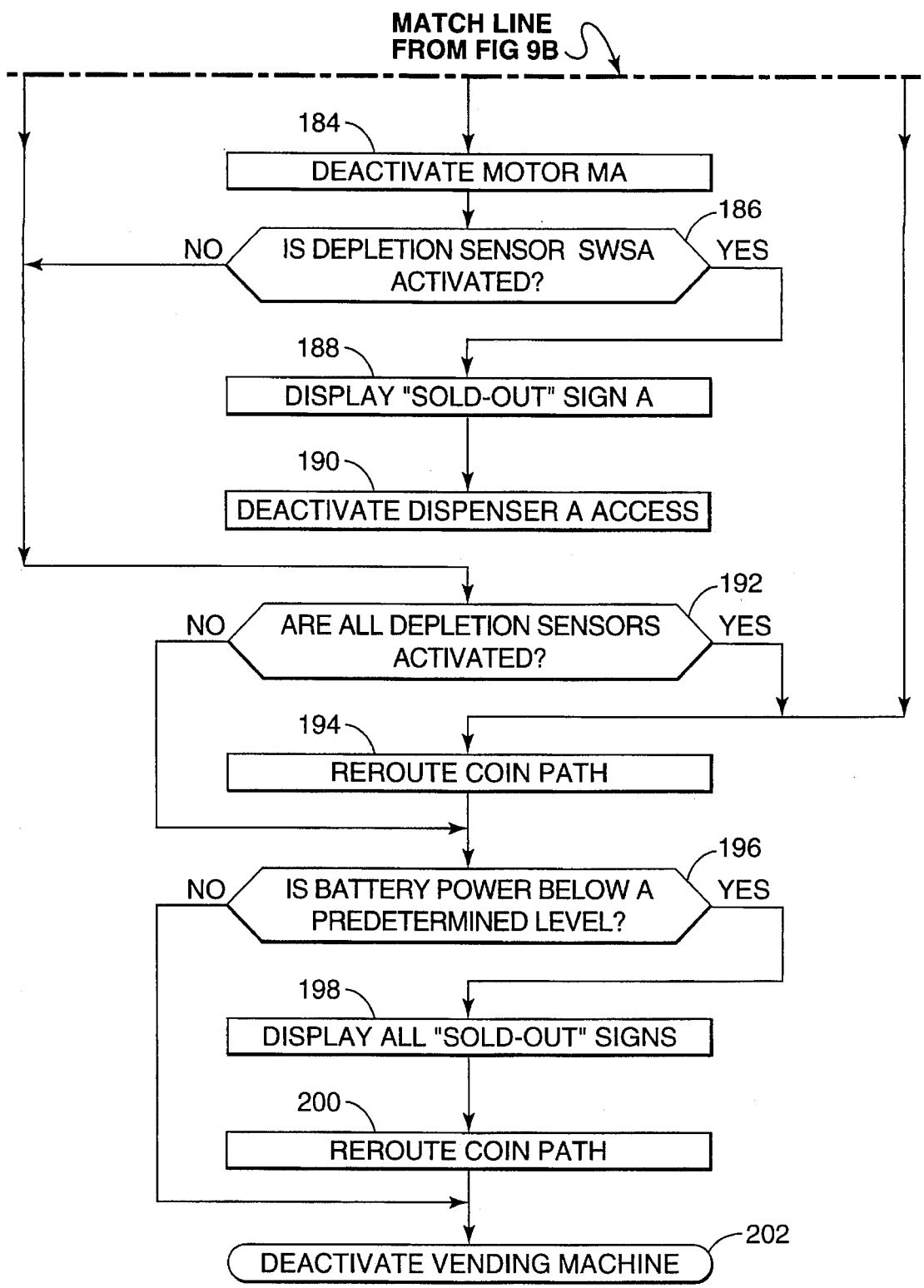

FIGS. 9A–C illustrate an operational flow chart of the microcontroller means illustrated in FIGS. 7 and 8A–8C of vending machine 2. Start box 140 indicates a user inserting the appropriate amount of change through coin slot 22 of the vending machine. Upon currency insertion, a cradle sorts the currency appropriately as indicated in action box 142. Depending upon the position of dual position slide switch SW1, the vending machine will activate itself in response to the receipt of the appropriate amount of change or currency, as seen in action box 144. For example, the switch may have a first setting for activating the microcontroller in response to receiving one coin and a second setting for activating the microcontroller for receiving several coins (e.g. quarters). When the vending machine receives the appropriate amount of change (e.i. SWCOIN has been closed the appropriate number of times) the vending machine becomes activated and waits for further input data.

Next, as seen in question box 146, the microcontroller may wait after coin insertion or detect a coin insertion problem as seen in question box 146. For instance, if SWCOIN remains closed, or if the user requires too much time, the microcontroller activates the coin slot solenoid CSN to reroute the coin path to return deposited money to the consumer. Thus, the microcontroller may wait for a predetermined amount of time as seen in action box 148 and then repeat the cycle until the consumer depresses a switch, the microcontroller detects a malfunction as discussed above, or the consumer waits too long to make a choice. If there is a malfunction, the microcontroller reroute the coin path via solenoid CSN to return inserted money, as seen in action box 194. Additionally, the microcontroller may then check the battery power level as seen in question box 196, reroute the coin path if not already rerouted, and deactivate the vending machine, as seen in boxes 198, 200, and 202.

Next, the microcontroller receives a signal from one of selector switches SWGA, SWGB, or SWGC as seen in question boxes 150, 152, or 154. For instance, if a consumer depresses button 32, SWGC sends a signal to activate motor C for plunger dispenser 48 as seen in FIG. 1. The motor MC which displaces the dispenser plunger. When the travel sensor SMWC has been activated an appropriate number of times, the plunger has performed a complete cycle and the microcontroller deactivates motor MC as seen in boxes 160 and 162.

Additionally, the microcontroller may also periodically check for a dispensing malfunction immediately after activation of a dispensing motor for any of the dispensers before preceding to wait box 158. An example of such malfunctions may be power surges associated with a dispenser motor straining to operate a jammed dispenser, etc. If the microprocessor detects such a malfunction, then the microcontroller may activate the "sold-out" sign for that dispenser, deactivate access to that dispenser, and activate solenoid CSN to return the inserted money to the consumer, if possible.

Next, the microcontroller checks to see if the depletion sensor SWSC is activated, as seen in box 164. If the depletion sensor SWSC detects that products in the column above dispenser 48 are depleted, then the microcontroller displays the "sold-out" sign C for that dispenser, deactivates access to dispenser 48, checks battery power, and deactivates the vending machine as seen in boxes 166, 168, 196, and 202. If sensor SWSC does not detect product depletion, then the microcontroller does not activate a "sold-out" sign, but checks battery power and then deactivates the vending machine.

The above-mentioned process is implemented for each of the dispensing mechanisms. Therefore, if a consumer presses select button 34 to activate dispenser 46, the microcontroller activates motor MB, as seen in box 170. As motor MB actuates rotor 130 to dispense a single product, the microcontroller checks to see if sensor SWMB has been activated by a predetermined number of times, as seen in box 172. If not, the microcontroller waits and continues to check, if so, the microcontroller deactivates motor MB. For example, as seen in FIG. 5 when motor 118 rotates rotor 130 approximately 180 degrees, one of protrusions 128 contacts switch 140, switch 140 signals the control means to deactivate motor 118, as seen in boxes 170 and 170–173 of FIG. 9B.

Next, the microcontroller checks to see if depletion sensor SWSB is activated. For example if the depletion sensor 136 in FIG. 5 indicates that no products are left in compartment 56, the microcontroller displaces a "sold-out" sign B or sign 12 in FIG. 1 deactivates dispenser B access (or access to rotary dispenser 46 in the preferred embodiment), and then proceeds through the routine of boxes 192–202 as was described above.

Finally, if a consumer depresses button 36 to close select switch SWGA, the microcontroller activates motor MA within the control scheme (i.e. a motor within plunger dispenser 44), as seen in boxes 146 and 180. The microcontroller sends a signal to activate motor A for plunger dispenser 44 as seen in FIG. 1. The motor MA then displaces the dispenser plunger. When the travel sensor SMWA has been activated an appropriate number of times, the plunger has performed a complete cycle and the microcontroller deactivates motor MC as seen in boxes 182, 184, and 185.

Next, the microcontroller checks to see if the depletion sensor SWSA is activated, as seen in box 186. If the depletion sensor SWSA detects that products in the column above dispenser 444 are depleted, then the microcontroller displays the "sold-out" sign A (e.g. sign 12 in FIG. 1) for that dispenser, deactivates access to dispenser 44, checks battery power, and deactivates the vending machine as seen in boxes 188, 190, 196, and 202. If sensor SWSA does not detect product depletion, then the microcontroller does not activate a "sold-out" sign, but checks battery power and then deactivates the vending machine.

It should be understood that various changes to the present invention may be made by the ordinarily skilled artisan, without departing from the spirit and scope of the present invention which is presented in the claims below. For example, the ordinarily skilled artisan will understand that above control scheme may be implemented for any number or specific type of dispensing mechanisms. Additionally, the ordinarily skilled artisan may employ any type of sensor to detect coin insertion, product depletion, or motor movement for dispenser control to accomplish the specific purposes of the present invention. The ordinarily skilled artisan will understand that this disclosure presents an example of the invention and is not meant to limit the invention, as presented in the claims, in any way whatsoever.

What is claimed is:

1. A vending machine for dispensing a product comprising:
    a first gravity feed compartment adapted to store products in a stack;
    a rotary dispenser positioned below said first compartment, wherein said rotary dispenser is adapted to accept and rotatingly dispense products from said first compartment;
    a second gravity feed compartment adapted to store products in a stack;
    a first plunger dispenser positioned below said second compartment, wherein said plunger dispenser is adapted to laterally displace products from said second compartment;
    control means for initiating product dispense cycles in each of said dispensers;
    means for accepting currency for a product; and
    a currency sensor adapted to send a currency signal to said control means when a predetermined amount of currency has been detected.

2. The vending machine of claim 1 wherein
    said means for accepting currency includes a currency slot.

3. The vending machine of claim 1 further comprising:
    a first selector switch associated with said plunger dispenser, wherein said first selector switch is adapted to send a dispense signal to said control means for activating said plunger dispenser; and
    a second selector switch associated with said rotary dispenser, wherein each said second selector switch is adapted to send a dispense signal to said control means for activating said rotary dispenser.

4. The vending machine of claim 1 wherein said vending machine further comprises:
    at least one selector switch associated with said dispensers, wherein said at least one selector switch is adapted to send a dispense signal to said control means for activating one of said dispensers to dispense product.

5. The vending machine of claim 4 wherein said control means is responsive to said dispense signal and said currency signal for initiating a dispense cycle.

6. The vending machine of claim 1 further comprising:
    a common dispensing chamber for receiving objects from each of said dispensers.

7. The vending machine of claim 6 wherein said first plunger dispenser further comprises:
    a plunger for laterally engaging and displacing a bottommost product from said first compartment into said dispensing chamber during a dispense cycle;
    a laterally collapsible mechanical linkage coupled to said plunger; and
    a motor coupled to said linkage adapted to collapse and expand said linkage during a dispense cycle to reciprocate said plunger.

8. The vending machine of claim 6 wherein said rotary dispenser further comprises:
    a cylindrical rotor adapted to receive products from said first compartment and for dispensing
    products into said dispensing chamber during a dispense cycle; and a motor adapted to rotate said rotor during a dispense cycle.

9. The vending machine of claim 6 further comprising:

a third gravity feed compartment adapted to store products in a stack; and a second plunger dispenser positioned below said third compartment, wherein said second plunger dispenser is adapted to laterally displace products from said second compartment.

10. The vending machine of claim 9 wherein said dispensing chamber further comprises:

two side walls disposed opposite one another, wherein each said sidewall includes
one of said first and second plunger dispensers disposed on an outside portion thereof,
a side wall aperture adapted to receive a product from one of said first and second plunger dispensers;

a bottom wall;

a top portion defined by said rotary dispenser; and a front opening adapted to allow a consumer to obtain a dispensed product from said chamber.

11. The vending machine of claim 9 wherein:

said means for accepting currency includes a currency slot.

12. The vending machine of claim 11 further comprising:

a first selector switch associated with said first plunger dispenser, wherein said first selector switch is adapted to send a dispense signal to said control means for activating said first plunger dispenser;

a second selector switch associated with said second plunger dispenser, wherein said second selector switch is adapted to send a dispense signal to said control means for activating said second plunger dispenser; and a third selector switch associated with said rotary dispenser, wherein said third selector switch is adapted to send a dispense signal to said control means for activating said rotary dispenser.

13. The vending machine of claim 12 wherein said control means is responsive to each of said dispense signals and said currency signal for initiating a dispense cycle in one of said first, second, or rotary dispensers which corresponds with a depressed one of said first, second or third selector switches, respectively.

14. The vending machine of claim 13 wherein said control means is responsive to depletion signals from all of said depletion sensors for activating means for blocking said coin slot.

15. A vending machine for dispensing a product comprising:

a first gravity feed compartment adapted to store products in a stack;

a rotary dispenser positioned below said first compartment, wherein said rotary dispenser is adapted to accept and rotatingly dispense products from said first compartment;

a second gravity feed compartment adapted to store products in a stack;

a first plunger dispenser positioned below said second compartment, wherein said plunger dispenser is adapted to laterally displace products from said second compartment;

control means for initiating product dispense cycles in each of said dispensers; and a depletion sensor in each said dispenser for detecting product depletion and for sending a product depletion signal from a depleted dispenser to said control means.

16. The vending machine of claim 15 further comprising a "sold-out" sign for each said dispenser within said vending machine.

17. The vending machine of claim 15 wherein said control means is responsive to depletion signals from all of said depletion sensors for deactivating said vending machine.

18. The vending machine of claim 15 wherein said control means is adapted to sample each of said depletion sensors after initiating a product dispense cycle in a dispenser.

19. The vending machine of claim 18 wherein said control means is responsive to each said depletion signal for deactivating a depleted dispenser associated with said depletion signal.

20. The vending machine of claim 19 wherein said control means is responsive to each said depletion signal for activating means for displaying a "sold-out" sign.

21. The vending machine of claim 19 wherein said control means is responsive to each said depletion signal from each said depletion sensor for displaying said "sold-out" sign associated with each said dispenser.

* * * * *